US012708622B2

(12) United States Patent
Hirbe et al.

(10) Patent No.: US 12,708,622 B2
(45) Date of Patent: Aug. 18, 2026

(54) METHODS OF TREATING CANCER AND INHIBITING TYK2 AND MEK

(71) Applicants: Angela Hirbe, St. Louis, MO (US); Dana Borcherding, St. Louis, MO (US); Neha Amin, St. Louis, MO (US)

(72) Inventors: Angela Hirbe, St. Louis, MO (US); Dana Borcherding, St. Louis, MO (US); Neha Amin, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 18/053,935

(22) Filed: Nov. 9, 2022

(65) Prior Publication Data

US 2023/0147873 A1 May 11, 2023

Related U.S. Application Data

(60) Provisional application No. 63/277,331, filed on Nov. 9, 2021.

(51) Int. Cl.
*A61K 31/501* (2006.01)
*A61K 31/166* (2006.01)
*A61P 35/00* (2006.01)

(52) U.S. Cl.
CPC .......... *A61K 31/501* (2013.01); *A61K 31/166* (2013.01); *A61P 35/00* (2018.01)

(58) Field of Classification Search
CPC ...... A61K 31/501; A61K 31/166; A61P 35/00
See application file for complete search history.

(56) References Cited

U.S. PATENT DOCUMENTS 10,023,571 B2 7/2018 Masse et al.
2018/0200378 A1 7/2018 Bennett et al.

OTHER PUBLICATIONS

Wu, Future Neurology, vol. 14, FNL7 (Year: 2019).*
Qin, Cancer Med., 2019, vol. 8, No. 11, pp. 5232-5241 (Year: 2019).*
Nagabushan, Precision Oncology, 2021, 9, published online Feb. 12, 2021 (Year: 2021).*
Kim, Current Dermatology Reports, 2021, 10:1-5, published online Jan. 7, 2021 (Year: 2021).*
Mokhtari, Oncotarget, 2017, vol. 8 No. 23, pp. 38022-38043 (Year: 2017).*
Akahane (British Journal of Haematology, vol. 177, pp. 271-282, 2017) (Year: 2017).*
Quereshy, J. Cancer Metastasis Treat. 2020; 6 (Year: 2020).*
Barbie, Clinical Lung Cancer, 2018, vol. 19, Iss. 6 (Year: 2018).*
Ostojic, Future Oncol. 2011, 7(9): 1035-1043 (Year: 2011).*
Xu, Expert Opinion of Pharmacotherapy, 20:16, 1943-1951, 2019 (Year: 2019).*
Akahane, British Journal of Haematology, 2017, 177, 271-282 (Year: 2017).*
Agrawal et al. (2020) JAK Inhibitors Safety in Ulcerative Colitis: Practical Implications. J Crohns Colitis. vol. 14, Supplement 2, pp. S755-S760.
Akahane et al. (2017) Anti-leukaemic activity of the TYK2 selective inhibitor NDI-031301 in T-cell acute lymphoblastic leukaemia. Br J Haematol. vol. 177, No. 2, pp. 271-282.
Andreoli et al. (2013) Clinical Resistance to Ruxolitinib is More Frequent In Patients Without MPN-Associated Mutations and is Rarely Due to Mutations in the JAK2 Kinase Drug-Binding Domain. Blood. vol. 122, No. 21, 6 pages.
Armstrong et al. (2022) Deucravacitinib versus placebo and apremilast in moderate to severe plaque psoriasis: efficacy and safety results from the 52-week, randomized, double-blinded, placebo-controlled phase 3 POETYK PSO-1 trial. J Am Acad Dermatol. vol. 88, No. 1, pp. 29-39.
Bhagwat et al. (2013) Sensitivity and resistance of JAK2 inhibitors to myeloproliferative neoplasms. Int J Hematol. vol. 97, No. 6, pp. 695-702.
Borcherding et al. (Aug. 2021) TYK2 in Cancer Metastases: Genomic and Proteomic Discovery. Cancers (Basel). vol. 13, No. 16, 4171, 20 pages.
Cai et al. (2020) Prognosis and risk factors for malignant peripheral nerve sheath tumor: a systematic review and meta-analysis. World J Surg Oncol. vol. 18, 257, 12 pages.
Carpenter et al. (2014) STAT3 Target Genes Relevant to Human Cancers. Cancers (Basel). vol. 6, No. 2, pp. 897-925.
Cervantes et al. (2013) Three-year efficacy, safety, and survival findings from COMFORT-II, a phase 3 study comparing ruxolitinib with best available therapy for myelofibrosis. Blood. vol. 122, No. 25, pp. 4047-4053.
Cervantes et al. (2017) Does ruxolitinib prolong the survival of patients with myelofibrosis? Blood. vol. 129, No. 7, pp. 832-837.
Chakraborty et al. (2016) Combination of JAK2 and HSP90 inhibitors: an effective therapeutic option in drug- resistant chronic myelogenous leukemia. Genes Cancer. vol. 7, No. 5-6, pp. 201-208.
Dehner et al. (Mar. 2021) Chromosome 8 gain is associated with high-grade transformation in MPNST. JCI Insight. vol. 6, No. 6, e146351, 15 pages.
Drake et al. (2013) Metastatic castration-resistant prostate cancer reveals intrapatient similarity and interpatient heterogeneity of therapeutic kinase targets. Proc Natl Acad Sci U S A. vol. 110, No. 49, pp. E4762-E4769.
Dry et al. (2010) Transcriptional pathway signatures predict MEK addiction and response to selumetinib (AZD6244). Cancer Res. vol. 70, No. 6, pp. 2264-2273.

(Continued)

*Primary Examiner* — Susanna Moore
*Assistant Examiner* — LuisAlberto Gonzalez

(57) ABSTRACT

Among the various aspects of the present disclosure is the provision of methods of treating cancer in a subject comprising administering a TYK2 inhibiting agent and a MEK inhibiting agent. In some embodiments, the subject has a malignant peripheral nerve sheath tumor (MPNST), neurofibromatosis Type 1 (NF1) cancer predisposition syndrome, benign plexiform neurofibromas (PN), or atypical neurofibromas (ANNUBP). Methods of inhibiting TYK2 and MEK in a subject in need thereof are also provided.

4 Claims, 32 Drawing Sheets
(32 of 32 Drawing Sheet(s) Filed in Color)

(56) References Cited

OTHER PUBLICATIONS

Endo et al. (2013) Prognostic significance of AKT/mTOR and MAPK pathways and antitumor effect of mTOR inhibitor in NF1-related and sporadic malignant peripheral nerve sheath tumors. Clin Cancer Res. vol. 19, No. 2, pp. 450-461.
Giordano et al. (2019) JAK/Stat5-mediated subtype-specific lymphocyte antigen 6 complex, locus G6D (LY6G6D) expression drives mismatch repair proficient colorectal cancer. J Exp Clin Cancer Res. vol. 38, 28, 11 pages.
González-Muñoz et al. (2022) The Need for New Treatments Targeting MPNST: The Potential of Strategies Combining MEK Inhibitors with Antiangiogenic Agents. Clin Cancer Res. vol. 28, No. 15, pp. 3185-3195.
Greenfield et al. (2018) The ruxolitinib effect: understanding how molecular pathogenesis and epigenetic dysregulation impact therapeutic efficacy in myeloproliferative neoplasms. J Transl Med. vol. 16, 360, 16 pages.
Groisberg et al. (2017) Clinical genomic profiling to identify actionable alterations for investigational therapies in patients with diverse sarcomas. Oncotarget. vol. 8, No. 24, pp. 39254-39267.
Harrison et al. (2012) JAK Inhibition with Ruxolitinib versus Best Available Therapy for Myelofibrosis. New Engl J Med. vol. 366, No. 9, pp. 787-798.
Harrison et al. (2020) Management of myelofibrosis after ruxolitinib failure. Ann Hematol. vol. 99, No. 6, pp. 1177-1191.
Harrison et al. (2020) Fedratinib in patients with myelofibrosis previously treated with ruxolitinib: An updated analysis of the JAKARTA2 study using stringent criteria for ruxolitinib failure. American Journal of Hematology. vol. 95, No. 6, pp. 594-603.
Hirbe et al. (2015) Whole Exome Sequencing Reveals the Order of Genetic Changes during Malignant Transformation and Metastasis in a Single Patient with NF1-plexiform Neurofibroma. Clin Cancer Res. vol. 21, No. 18, pp. 4201-4211.
Hirbe et al. (2017) Clinical genomic profiling identifies TYK2 mutation and overexpression in patients with neurofibromatosis type 1-associated malignant peripheral nerve sheath tumors. Cancer. vol. 123, No. 7, pp. 1194-1201.
Hirbe et al. (Mar. 2021) TYK2 as a biomarker and therapeutic target for NF1-associated Malignant Peripheral Nerve Sheath Tumors. Annual Report for U.S. Army Medical Research and Materiel Command. Retrieved from https://apps.dtic.mil/sti/pdfs/AD1129103.pdf on Dec. 6, 2023. 26 pages.
Hornakova et al. (2011) Oncogenic JAK1 and JAK2-activating mutations resistant to ATP-competitive inhibitors. Haematologica. vol. 96, No. 6, pp. 845-853.
Ianevski et al. (2020) SynergyFinder 2.0: visual analytics of multi-drug combination synergies. Nucleic Acids Res. vol. 48, No. W1, pp. W488-W493.
Koppikar et al. (2012) Heterodimeric JAK-STAT activation as a mechanism of persistence to JAK2 inhibitor therapy. Nature. vol. 489, No. 7414, pp. 155-159.
Levine et al. (2012) Combination Therapy Using JAK2 and HSP90 Inhibitors Increased Efficacy in Myelofibrosis in Vivo. Blood. vol. 120, No. 21, pp. 805.
Morales et al. (2019) MEK inhibition enhances the response to tyrosine kinase inhibitors in acute myeloid leukemia. Nat Sci Rep. vol. 9, No. 18630, 11 pages.
Organ et al. (2011) Quantitative phospho-proteomic profiling of hepatocyte growth factor (HGF)-MET signaling in colorectal cancer. J Proteome Res. vol. 10, No. 7, pp. 3200-3211.
Pollard et al. (2020) A clinically and genomically annotated nerve sheath tumor biospecimen repository. vol. 7, 184, 9 pages.
Pratilas et al. (2009) (V600E)BRAF is associated with disabled feedback inhibition of RAF-MEK signaling and elevated transcriptional output of the pathway. Proc Natl Acad Sci U S A. vol. 106, No. 11, pp. 4519-4524.
Qin et al. (2019) TYK2 promotes malignant peripheral nerve sheath tumor progression through inhibition of cell death. Cancer Med. vol. 8, No. 11, pp. 5232-5241.
Qureshy et al. (2020) Targeting the JAK/STAT pathway in solid tumors. J Cancer Metastasis Treat. vol. 6, 27, 26 pages.
Reader et al. (2019) Immunotherapeutic effects of the TYK2 inhibitor SAR-20351 in syngeneic tumor models. Molecular Cancer Therapeutics. vol. 18, Suppl 12, 2 pages.
Sanda et al. (2013) TYK2-STAT1-BCL2 pathway dependence in T-cell acute lymphoblastic leukemia. Cancer Discov. vol. 3, No. 5, pp. 564-577.
Song et al. (2008) Protein expression profiling of breast cancer cells by dissociable antibody microarray (DAMA) staining. Mol Cell Proteomics. vol. 7, No. 1, pp. 163-169.
Springworks Therapeutics, Inc. (2019) MEK Inhibitor Mirdametinib (PD-0325901) in Patients with Neurofibromatosis Type I Associated Plexiform Neurofibromas (ReNeu). Retrieved from https://clinicaltrials.gov/study/NCT03962543 on Dec. 7, 2023, 13 pages.
Stivala et al. (2019) Targeting compensatory MEK/ERK activation increases JAK inhibitor efficacy in myeloproliferative neoplasms. J Clin Invest. vol. 129, No. 4, pp. 1596-1611.
Tavakoli Shirazi et al. (May 2021) Constitutive JAK/STAT signaling is the primary mechanism of resistance to JAKi in TYK2-rearranged acute lymphoblastic leukemia. Cancer Lett. vol. 512, pp. 28-37.
Taylor PC. (2019) Clinical efficacy of launched JAK inhibitors in rheumatoid arthritis. Rheumatology. vol. 58, Suppl 1, pp. i17-i26.
Velusamy et al. (2014) A novel recurrent NPM1-TYK2 gene fusion in cutaneous CD30-positive lymphoproliferative disorders. Blood. vol. 124, No. 25, pp. 3768-3771.
Wang et al. (Feb. 2021) Activation of Receptor Tyrosine Kinases Mediates Acquired Resistance to MEK Inhibition in Malignant Peripheral Nerve Sheath Tumors. Cancer Res. vol. 81, No. 3, pp. 747-762.
Wrobleski et al. (2019) Highly Selective Inhibition of Tyrosine Kinase 2 (TYK2) for the Treatment of Autoimmune Diseases: Discovery of the Allosteric Inhibitor BMS-986165. J Med Chem. vol. 62, No. 20, pp. 8973-8995.
Wu et al. (2019) Therapeutic targets for malignant peripheral nerve sheath tumors. Future Neurology. vol. 14, FNL7, 12 pages.
Zhang et al. (2020) The Role of Polycomb Repressive Complex in Malignant Peripheral Nerve Sheath Tumor. Genes (Basel). vol. 11, No. 3, 287, 22 pages.
Zhao et al. (2020) Dual Inhibition of MAPK and JAK2/STAT3 Pathways Is Critical for the Treatment of BRAF Mutant Melanoma. Mol Ther Oncolytics. vol. 18, pp. 100-108.
Zhu et al. (2009) Proteomic identification of differentially-expressed proteins in squamous cervical cancer. Gynecol Oncol. vol. 112, pp. 1248-1256.
Akahane et al. 2017. Anti-leukaemic activity of the TYK2 selective inhibitor NDI-031301 in T-cell acute lymphoblastic leukaemia. British Journal of Haematology, vol. 177, pp. 271-282.
Carmo et al. 2011. A novel requirement for Janus kinases as mediators of drug resistance induced by fibroblast growth factor-2 in human cancer cells. PLoS One, vol. 6(5), article No. e19861.
ÜBEL et al. 2013. Establishing the role of tyrosine kinase 2 in cancer. Oncoimmunology, vol. 2(1), article No. e22840.

* cited by examiner

TYK2 Immunohistochemistry (IHC)

| Tumor Type | Weak TYK2 (<2) | Strong TYK2 ($\geq$2) |
|---|---|---|
| MPNST (all) | 49 (44%) | 63 (56%) |
| MPNST: NF1 | 33 (47%) | 37 (53%) |
| MPNST: Sporadic | 16 (38%) | 26 (62%) |
| Plexiform NF | 26 (67%) | 13 (33%) |

| | Weak TYK2 (<2) | Strong TYK2 (≥2) |
|---|---|---|
| MPNST (all) | 22 (44%) | 28 (56%) |
| MPNST: NF1 | 11 (39%) | 17 (61%) |
| MPNST: Sporadic | 11 (50%) | 11 (50%) |
| Plexiform Neuro. | 26 (67%) | 13 (33%) |
| ANNUBP | 2 (8%) | 22 (92%) |

METHODS OF TREATING CANCER AND INHIBITING TYK2 AND MEK

CROSS-REFERENCE TO RELATED APPLICATIONS

This application claims priority from U.S. Provisional Application Ser. No. 63/277,331 filed on 9 Nov. 2021, which is incorporated herein by reference in its entirety.

STATEMENT REGARDING FEDERALLY SPONSORED RESEARCH OR DEVELOPMENT

This invention was made with government support under W81XWH-20-1-0148 awarded by the U.S. Army Medical Research and Materiel Command (ARMY/MRMC). The government has certain rights in the invention.

MATERIAL INCORPORATED-BY-REFERENCE

Not applicable.

FIELD

The present disclosure generally relates to methods of treating cancer and inhibiting TYK2 and MEK using a combination of a TYK2 inhibitor and a MEK inhibitor.

SUMMARY

Among the various aspects of the present disclosure is the provision of methods for treating cancer or inhibiting TYK2 and MEK in a subject.

An aspect of the present disclosure provides for a method of treating cancer in a subject in need thereof comprising administering a therapeutically effective amount of a TYK2 inhibiting agent; and administering a therapeutically effective amount of a MEK inhibiting agent. In some embodiments, the subject has or is suspected of having a malignant peripheral nerve sheath tumor (MPNST). In some embodiments, the MPNST overexpresses TYK2 or comprises a TYK2 mutation. In some embodiments, the subject has or is suspected of having neurofibromatosis Type 1 (NF1) cancer predisposition syndrome, benign plexiform neurofibromas (PN), or atypical neurofibromas (ANNUBP). In some embodiments, the MEK inhibiting agent is mirdametinib. In some embodiments, the TYK2 inhibiting agent is TC-JL-37, a compound having a structure according to Formula I wherein R comprises an ethanesulfonamide, or a compound having a structure according to Formula II wherein R comprises an ethanesulfonamide. In some embodiments, the TYK2 inhibiting agent is WU-12 or WU-76. In some embodiments, the TYK2 inhibiting agent is deucravacitinib. In some embodiments, the TYK2 inhibiting agent does not inhibit JAK1, JAK2, or JAK3. In some embodiments, the TYK2 inhibiting agent and the MEK inhibiting agent are administered in an amount effective to synergistically reduce proliferation of cancer cells, increase apoptosis of cancer cells, or reduce tumor volume. In some embodiments, the method further comprises obtaining a biological sample from the subject and measuring expression of TYK2 in the biological sample.

Another aspect of the present disclosure provides for a method of inhibiting TYK2 and MEK in a subject in need thereof, the method comprising administering an effective amount of a TYK2 inhibiting agent; and administering an effective amount of a MEK inhibiting agent. In some embodiments, the subject has or is suspected of having cancer. In some embodiments, the subject has or is suspected of having a malignant peripheral nerve sheath tumor (MPNST). In some embodiments, the MPNST overexpresses TYK2 or comprises a TYK2 mutation. In some embodiments, the subject has or is suspected of having neurofibromatosis Type 1 (NF1) cancer predisposition syndrome, benign plexiform neurofibromas (PN), or atypical neurofibromas (ANNUBP). In some embodiments, the MEK inhibiting agent is mirdametinib. In some embodiments, the TYK2 inhibiting agent is TC-JL-37, a compound having a structure according to Formula I wherein R comprises an ethanesulfonamide, or a compound having a structure according to Formula II wherein R comprises an ethanesulfonamide. In some embodiments, the TYK2 inhibiting agent is WU-12 or WU-76. In some embodiments, the TYK2 inhibiting agent is deucravacitinib. In some embodiments, the TYK2 inhibiting agent does not inhibit JAK1, JAK2, or JAK3. In some embodiments, the TYK2 inhibiting agent and the MEK inhibiting agent are administered in an amount effective to synergistically reduce proliferation of cancer cells, increase apoptosis of cancer cells, or reduce tumor volume.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 1(A-D) is an exemplary embodiment showing TYK2 inhibitors reduce proliferation in MPNST cells in accordance with the present disclosure.

FIG. 2(A-B) is a series of graphs showing inhibition of TYK2 induces apoptosis in four MPNST cell lines.

FIG. 3(A-B) is a series of graphs showing TYK2 inhibitors reduce proliferation and induce apoptosis in additional MPNST cells.

or WU-76 (right panels) for 3 days. Percent cell confluence over time was determined by the IncuCyte live cell imaging assay. *P<0.0001 vs. control.

Figure 4A:
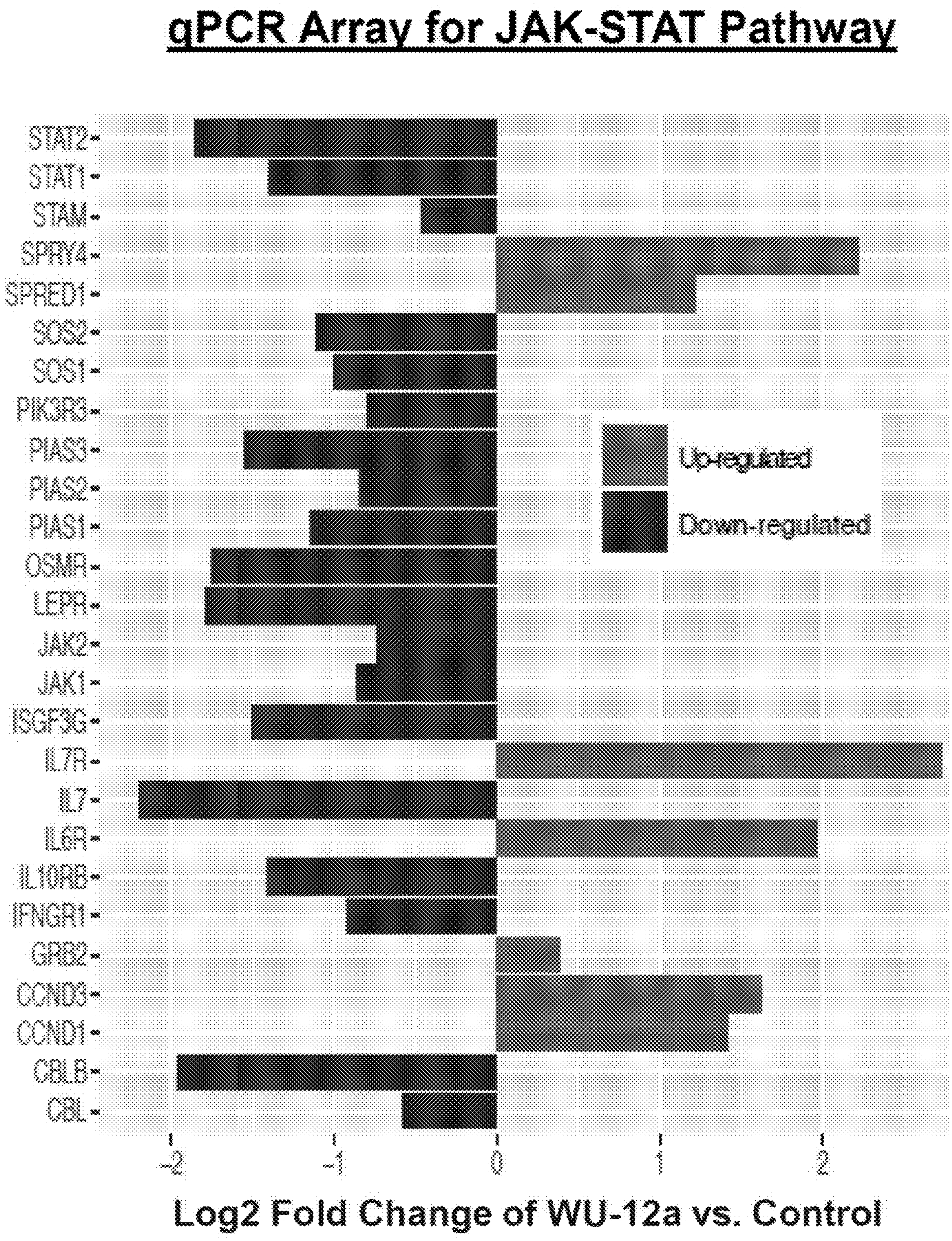
Figure 4B:
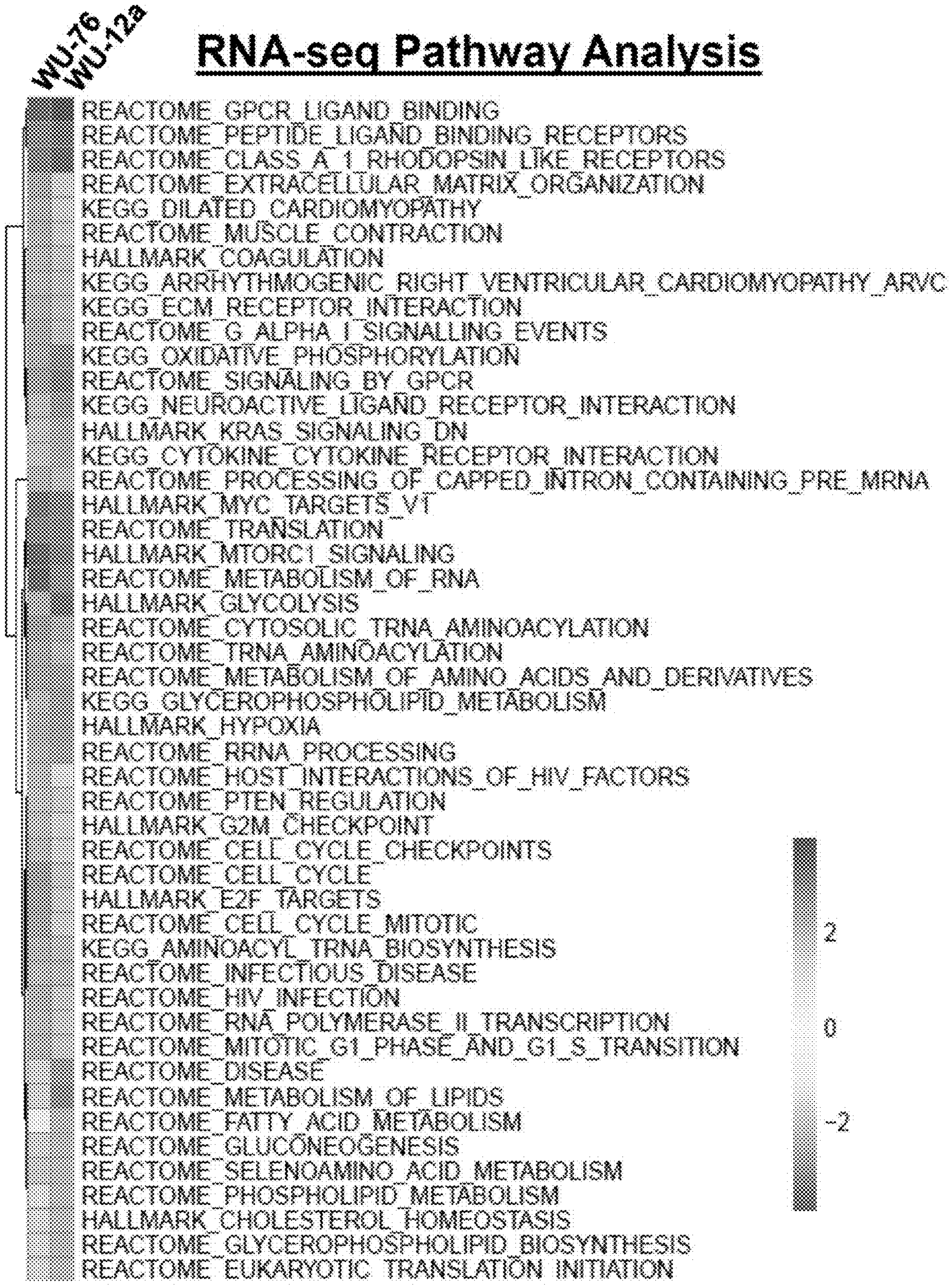

FIG. 4(A-B) is an exemplary embodiment showing TYK2 inhibition leads to compensatory stimulation of the MEK/MAP-kinase (MAPK) pathway in MPNST cells in accordance with the present disclosure. FIG. 4A is a bar graph showing gene expression change of JH-2-002 cells treated with 40 μM WU-12 for 48 hours. Gene expression was analyzed by qPCR array for JAK/STAT pathway related genes. $Log_2$ fold-change of significantly changed genes are graphed. P<0.05 vs. vehicle control. FIG. 4B is a heat map showing gene expression of JW23.3 cells treated with 40 μM WU-12 or WU-76 for 48 hours. Global gene expression was determined by RNA-seq pathway analysis.

Figure 5A:
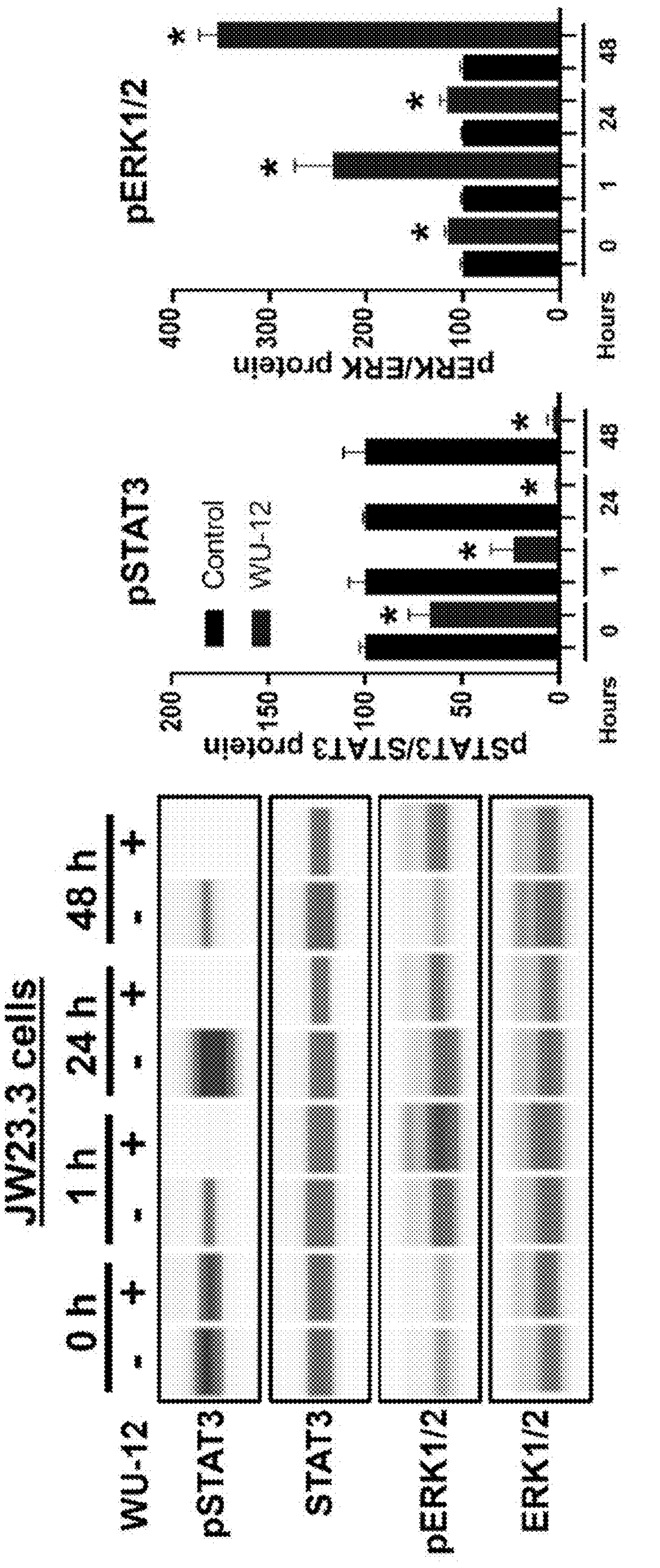
Figure 5B:
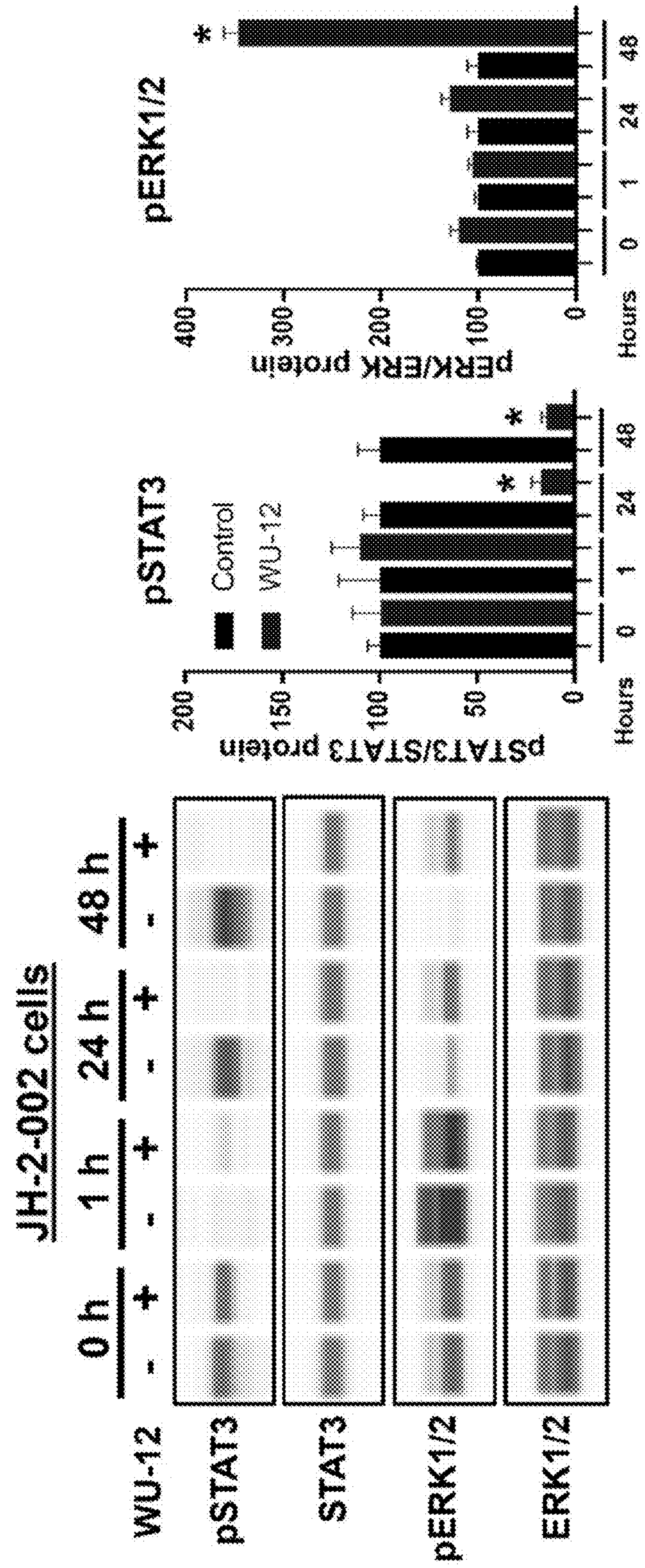
Figure 6A:
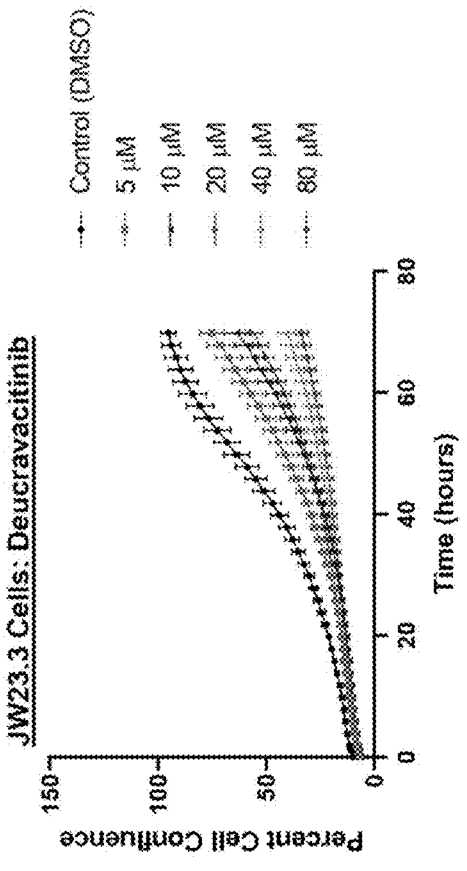
Figure 6B:
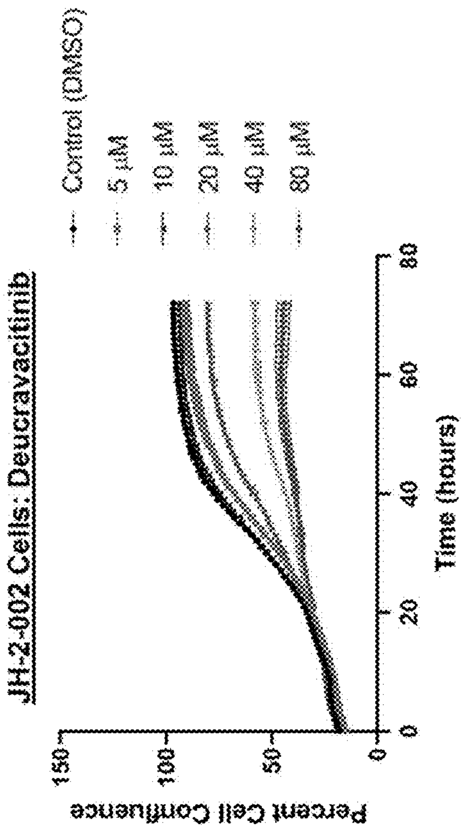
Figure 6C:
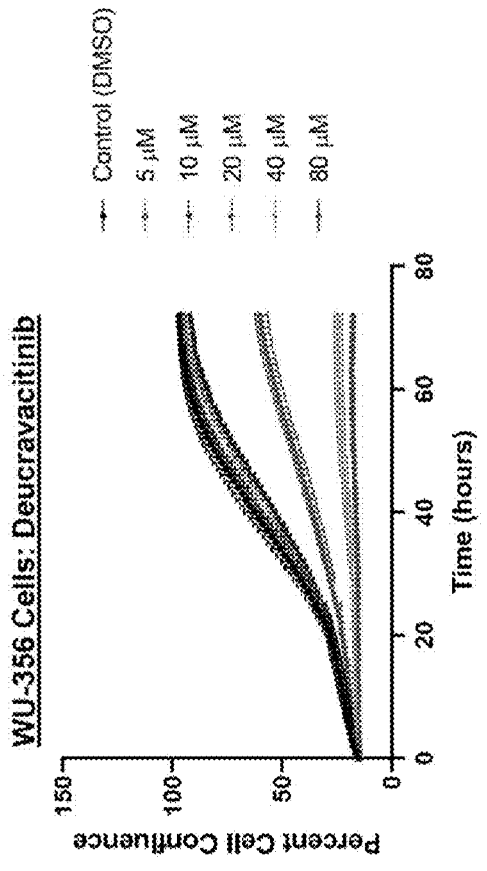
Figure 6D:
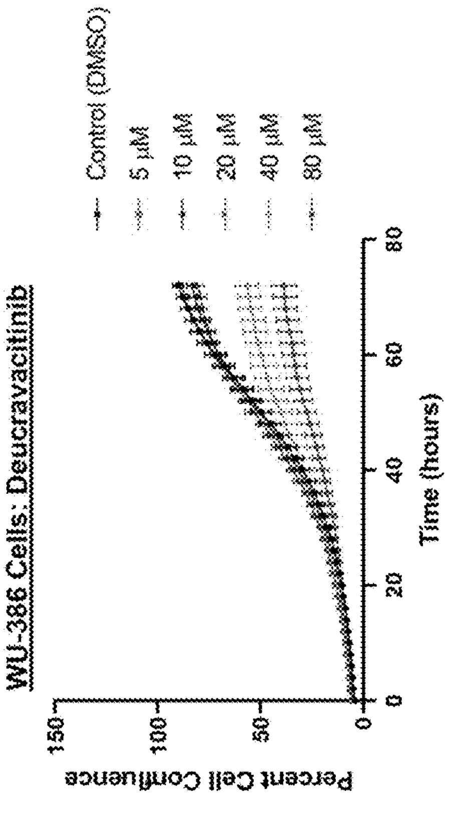

FIG. 5(A-B) includes images and bar graphs showing TYK2 inhibitory drugs decrease activation of STAT3 while increasing activation of ERK1/2 in MPNST cells in accordance with the present disclosure. FIG. 5A shows protein expression of JW23.3 cells and FIG. 5B shows protein expression of JH-2-002 cells incubated with a TYK2 inhibitor (40 μM WU-12) or vehicle control for the indicated times. Phosphorylated and total protein levels for STAT3, ERK1/2, and S6K were analyzed by the WES western system. Bands were analyzed by densitometry in the WES software, with phosphorylated protein normalized to the matching total protein and expressed as percent of control at the same time point. *P<0.05 vs. vehicle control at the same time point.

FIG. 6(A-D) is a series of graphs showing the specific TYK2 inhibitor, deucravacitinib (BMS-986165), decreases MPNST cell proliferation at lower doses. FIG. 6A shows confluence of JW23.3 cells, FIG. 6B shows confluence of JH-2-002 cells, FIG. 6C shows confluence of WU-356 cells, and FIG. 6D shows confluence of WU-386 cells treated with the indicated doses of the specific TYK2 inhibitor, deucravacitinib (BMS-986165), for 3 days in IncuCyte live cell assays, with YOYO-1 green fluorescence as an indicator of apoptosis.

Figure 7A:
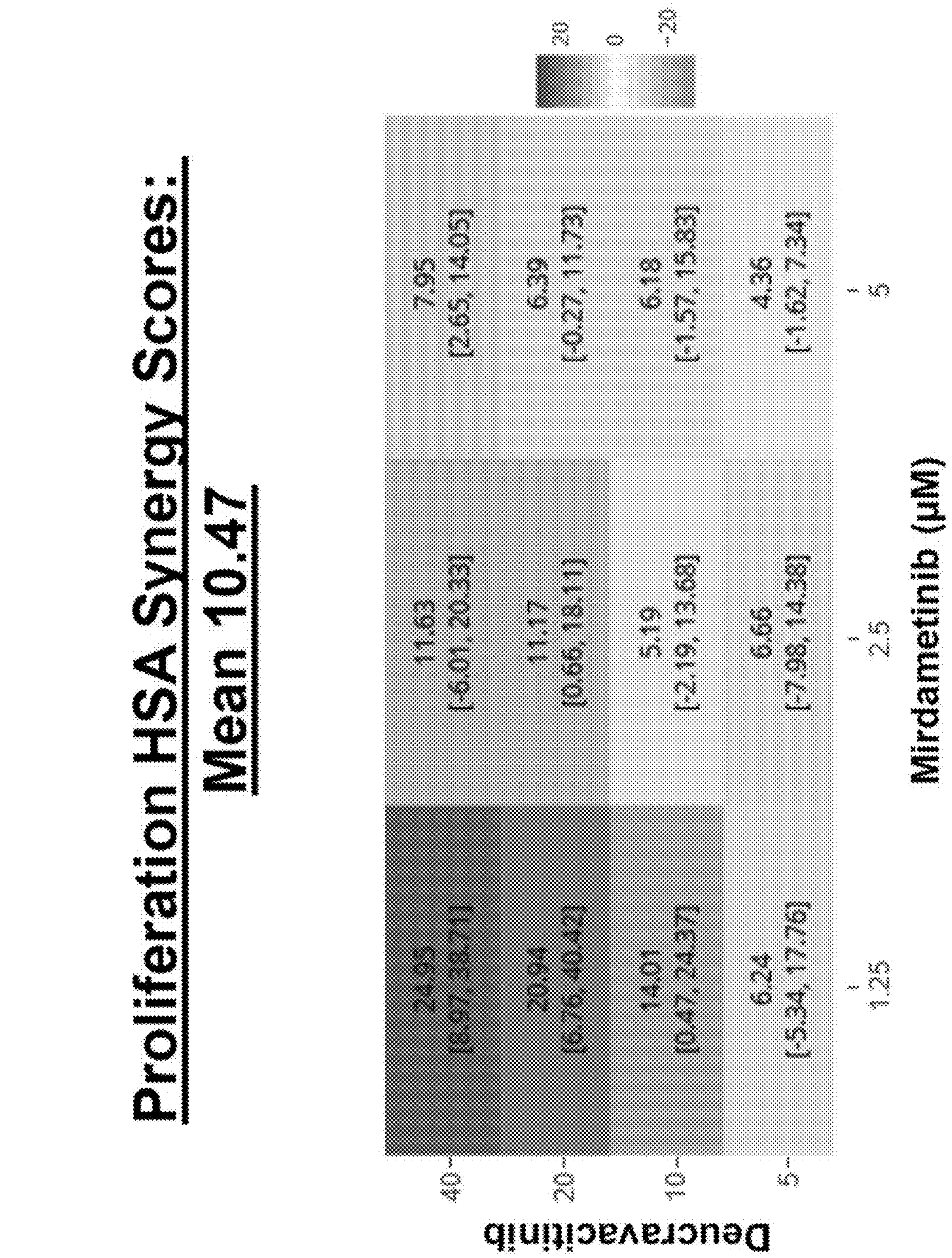
Figure 7B:
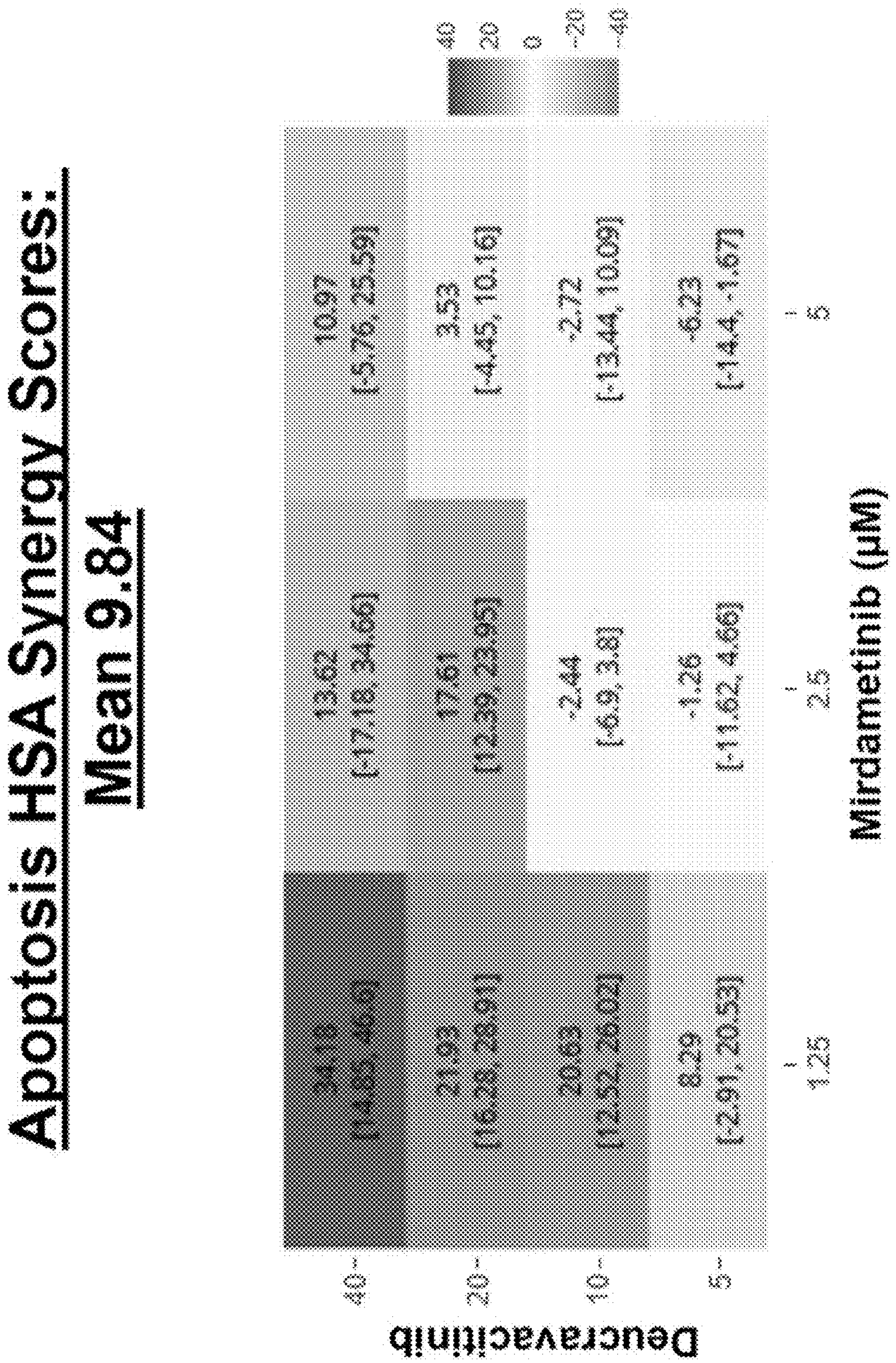
Figure 7C:
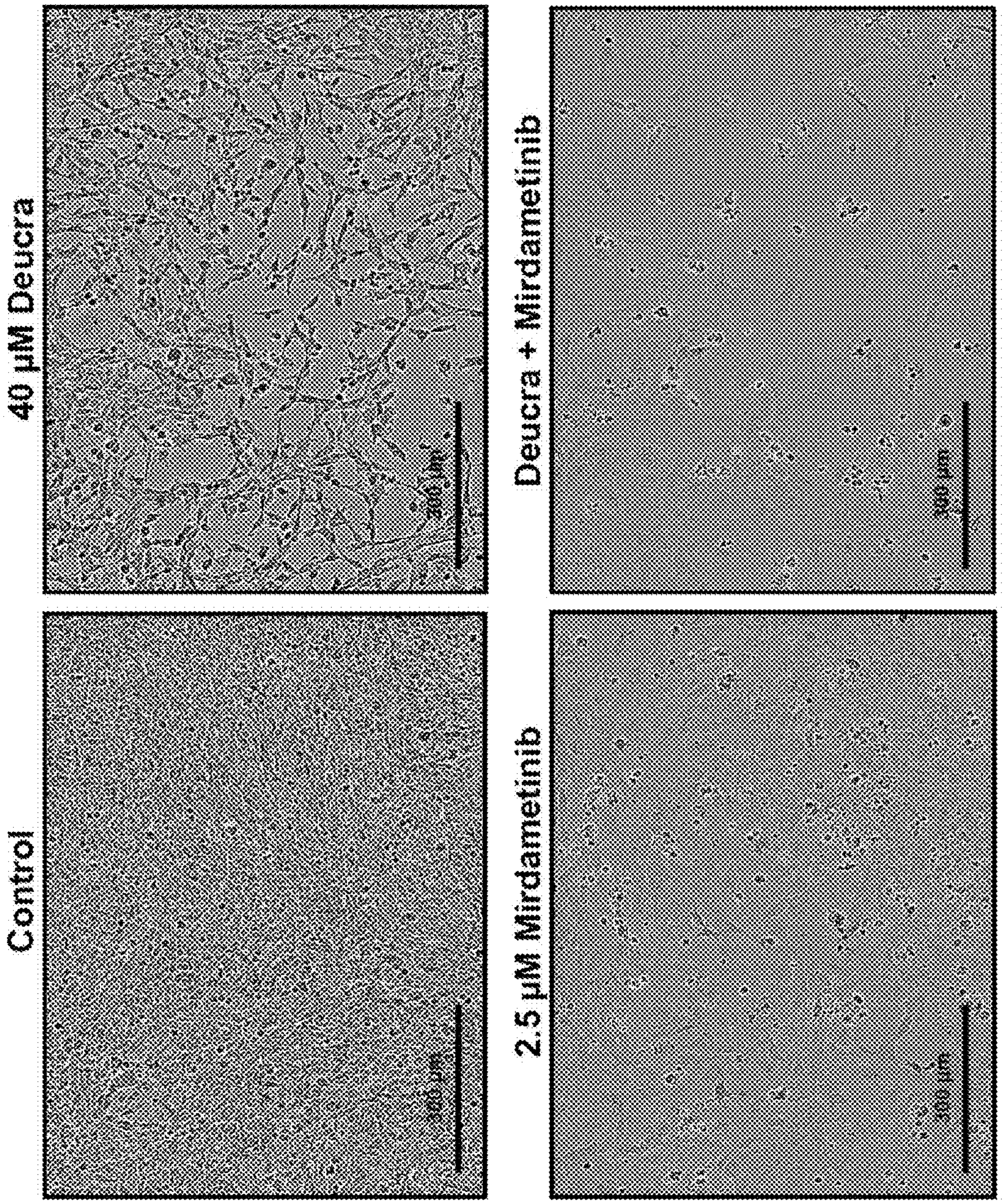

FIG. 7(A-C) is an exemplary embodiment showing inhibitors of TYK2 (deucravacitinib) and MEK (mirdametinib) act synergistically to reduce proliferation and increase apoptosis in JW23.3 MPNST cells in accordance with the present disclosure. Cell confluence and apoptosis were analyzed by the IncuCyte assay after 48-hour incubation with drugs. FIG. 7A is a table showing synergy scores of inhibition of cell proliferation and FIG. 7B is a table showing synergy scores of apoptosis. Synergy was analyzed using Synergy Finder software by the HSA method and mean synergy score is reported (P<0.05 vs. drug alone). Intensity of red color indicates synergy score for each dose combination, while green indicates antagonism. FIG. 7C shows representative images of JW23.3 cells treated for 48 hours. YOYO-1 green fluorescence indicates apoptotic cells.

Figure 8A:
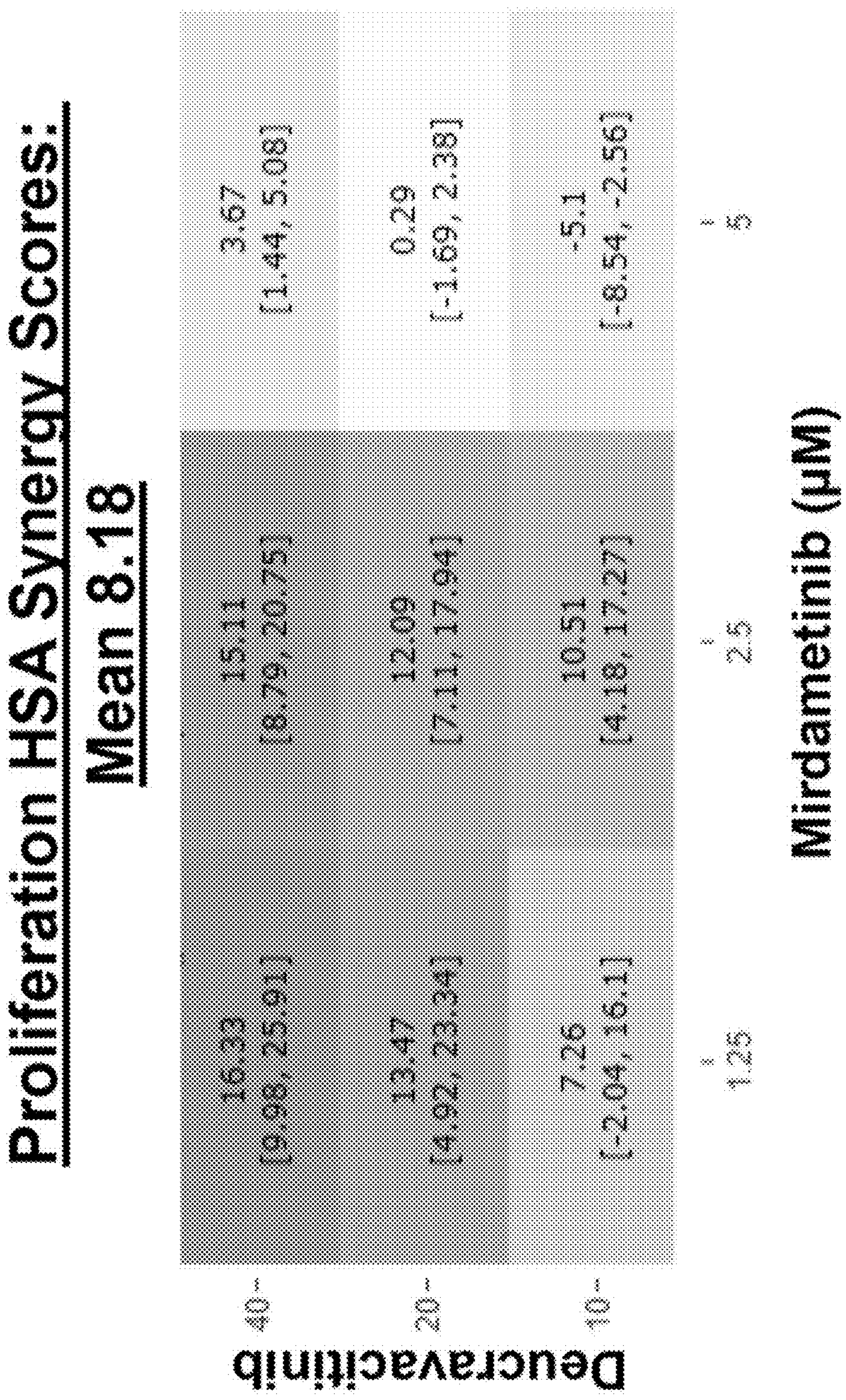
Figure 8B:
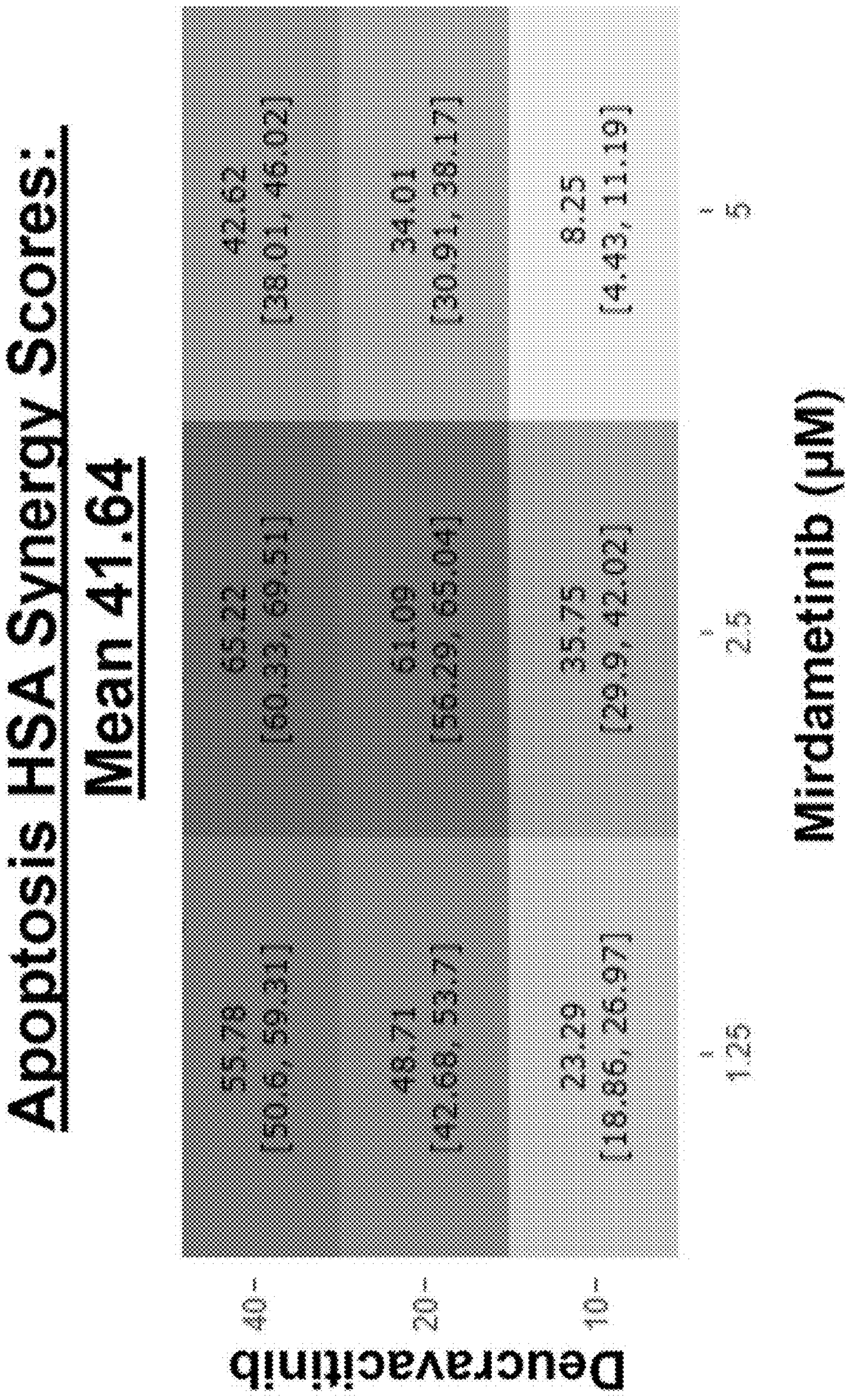
Figure 8C:
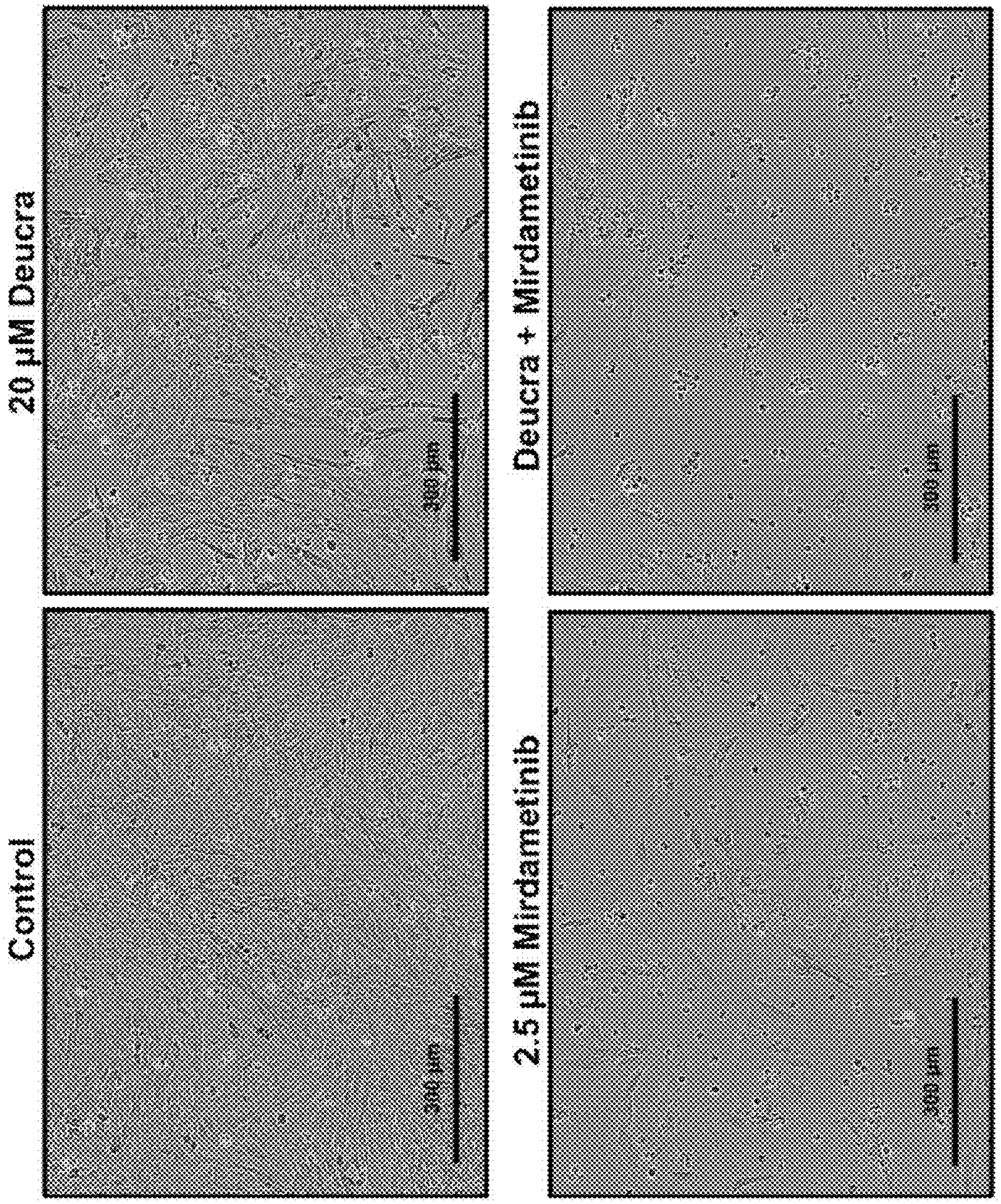

FIG. 8(A-C) is an exemplary embodiment showing inhibitors of TYK2 (deucravacitinib) and MEK (mirdametinib) act synergistically to reduce proliferation and increase apoptosis in JH 2-002 MPNST cells in accordance with the present disclosure. FIG. 8A is a table showing synergy scores for inhibition of cell proliferation and FIG. 8B is a table showing synergy scores for apoptosis. Cell proliferation and cell death were determined by the IncuCyte assay after 72-hour treatment. Synergy was analyzed using Synergy Finder software by the HSA method. Mean synergy score was calculated (P<0.05 vs. drug alone). Intensity of red color indicates synergy, while green indicates antagonism, for each dose combination. FIG. 8C shows representative images of JH 2-002 cells treated with the indicated doses for 72 hours. Apoptotic cells are stained with YOYO-1 green fluorescence dye.

Figure 9A:
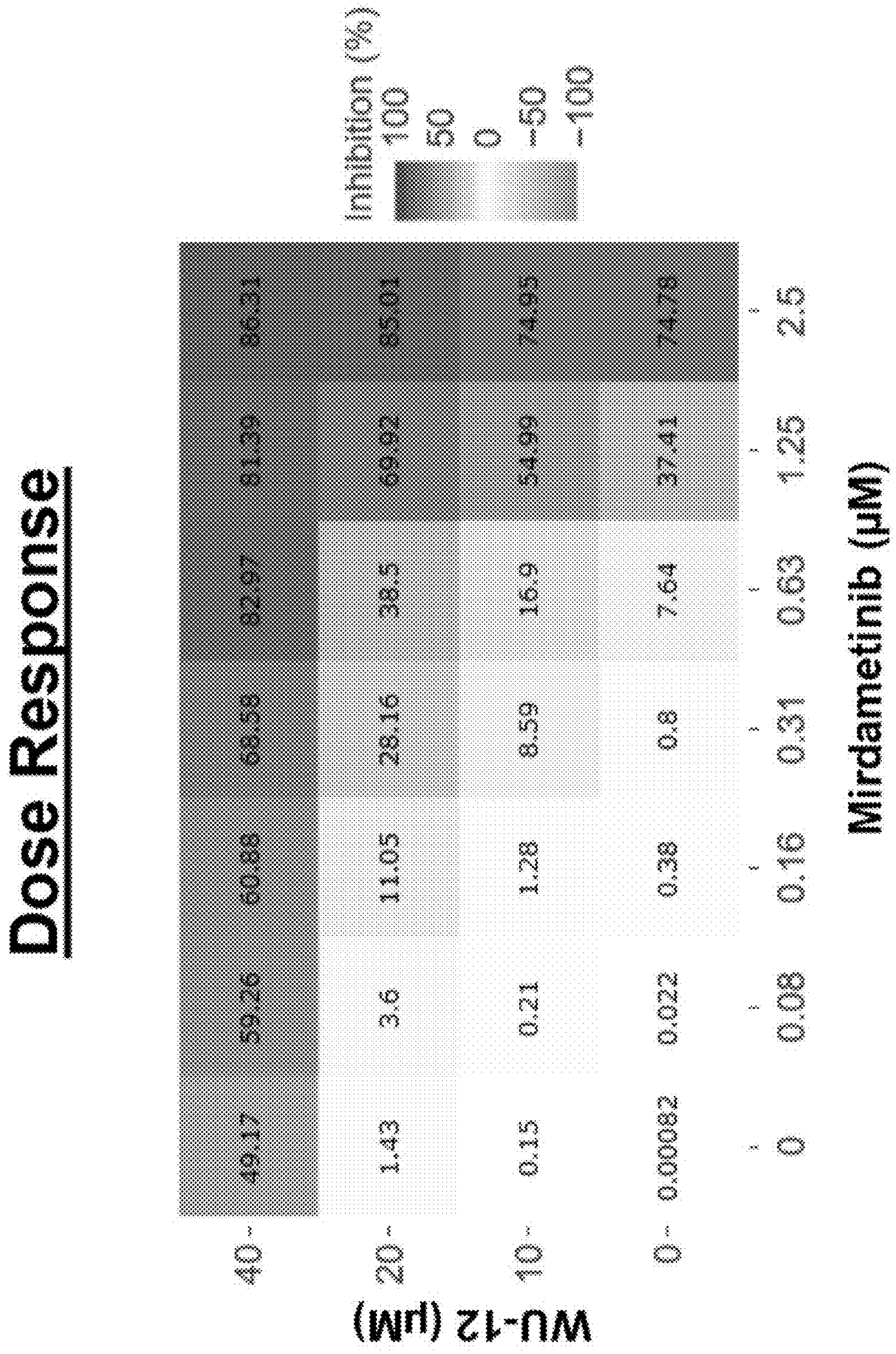
Figure 9B:
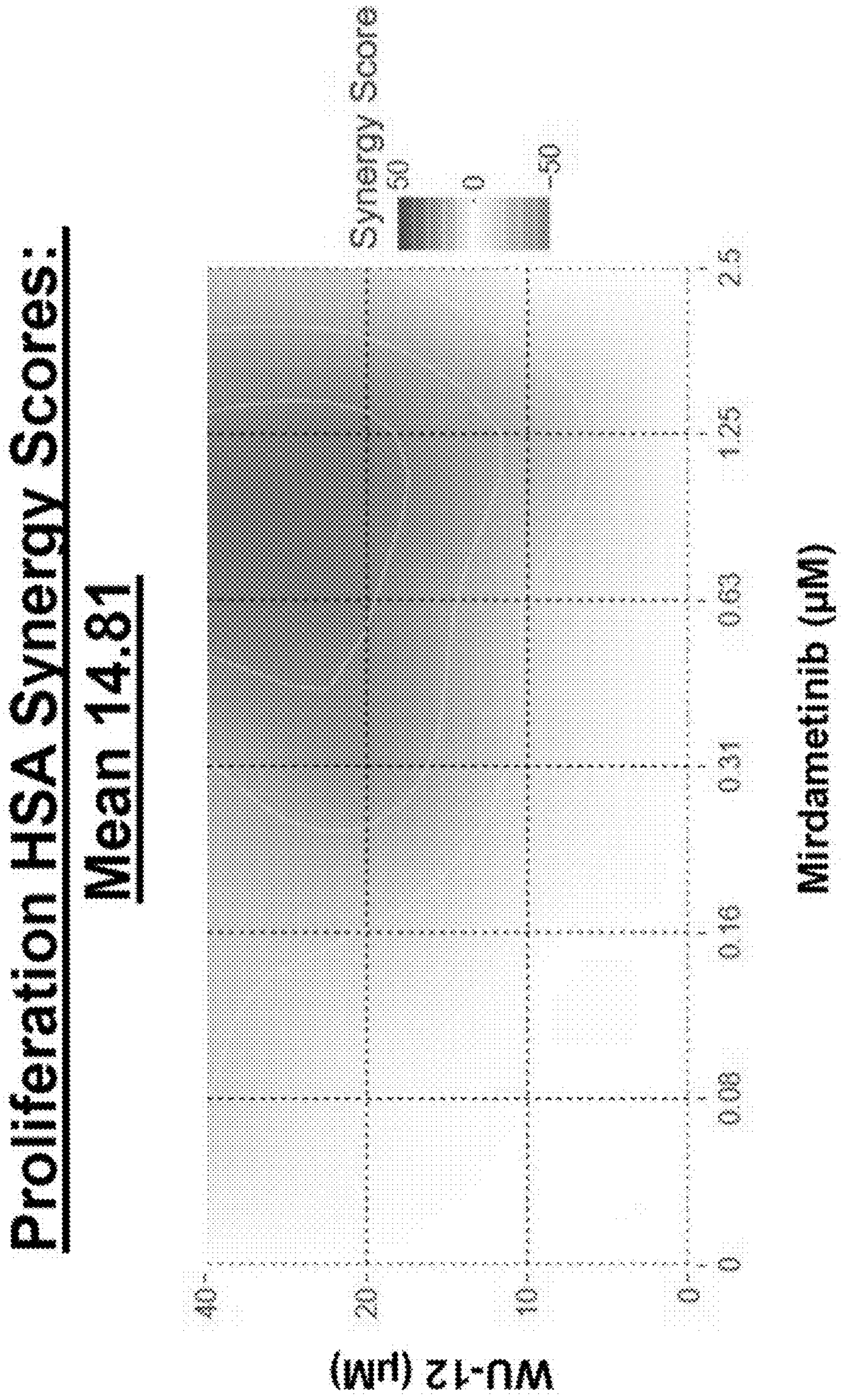
Figure 9C:
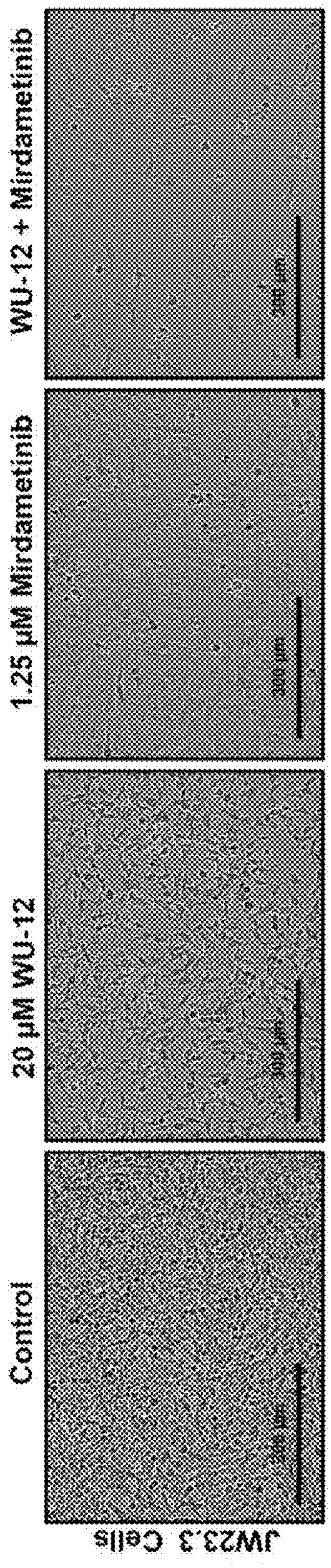

FIG. 9(A-C) is an exemplary embodiment showing inhibitors of TYK2 (WU-12) and MEK (mirdametinib) act synergistically to reduce proliferation in JW23.3 MPNST cells in accordance with the present disclosure. Cell confluence was analyzed by IncuCyte assay after 72-hour incubation with drugs. FIG. 9A is a table showing percent inhibition dose response calculated for each drug combination by Synergy Finder. FIG. 9B is a table showing synergistic effect of the drug combination on proliferation determined using the HSA method. FIG. 9C shows representative images of JW23.3 cells treated for 48 hours. YOYO-1 green fluorescence indicates apoptotic cells.

FIG. 10(A-D) is an exemplary embodiment showing the combination of drugs inhibiting TYK2 and MEK block MPNST tumor growth in mice in accordance with the present disclosure. FIG. 10A is a schematic diagram of treatment paradigm. FIG. 10B is a graph showing tumor volume in mice with JW23.3 MPNST xenograft tumors, FIG. 10C is a graph showing tumor volume in mice with WU-386 MPNST PDX tumors, and FIG. 10D is a graph showing tumor volume in mice with JH-2-002 MPNST xenograft tumors treated daily with 1.5 mg/kg deucravacitinib (Deucra, BMS-986165), 30 mg/kg mirdametinib (Mirda), the combination of drugs, or vehicle control for three weeks or until tumors reached the maximum allowed volume. *P<0.05 vs. vehicle control. [a] P<0.05 for drug combination vs. drugs alone.

Figure 11A:
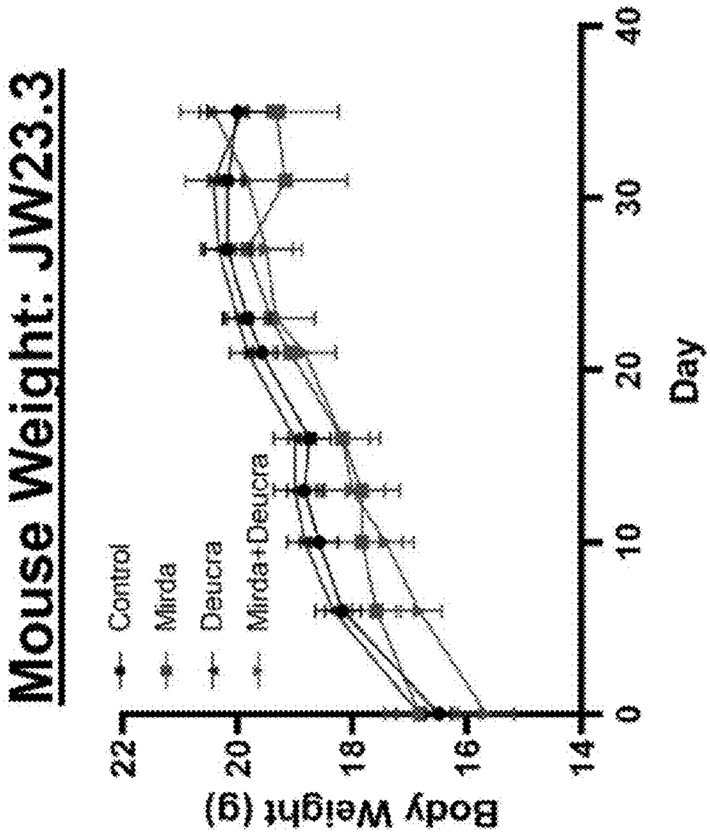
Figure 11B:
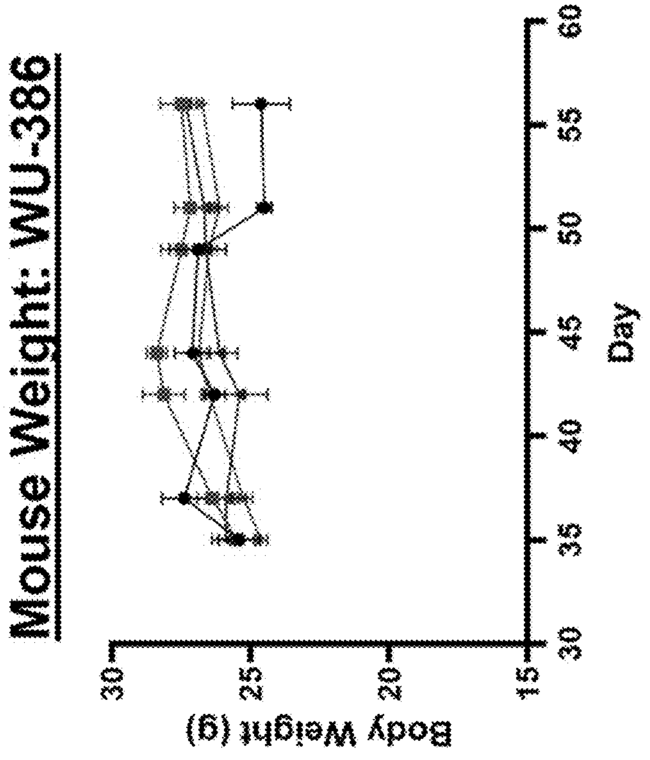
Figure 11C:
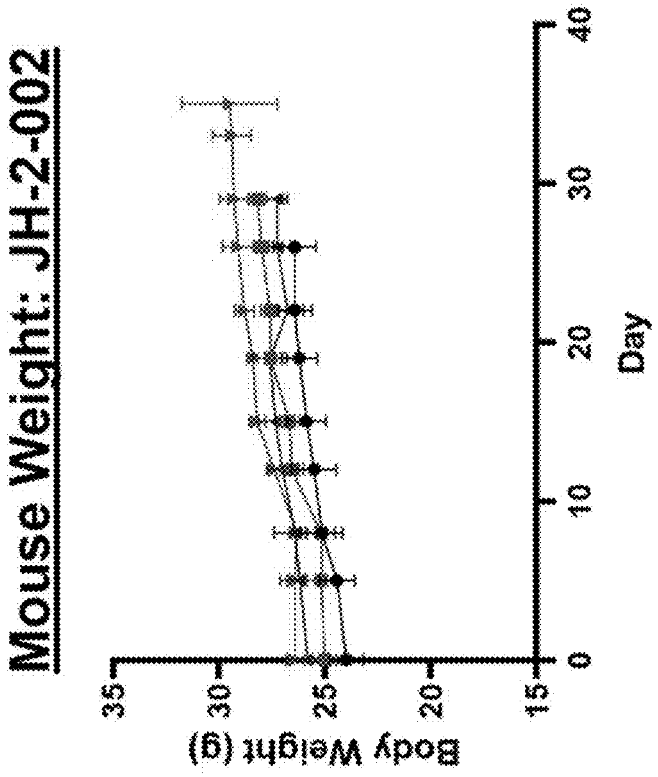

FIG. 11(A-C) is a series of graphs showing treatment with deucravacitinib and/or mirdametinib did not significantly decrease mouse body weight over time. FIG. 11A shows weight of mice implanted with JW23.3 cells. FIG. 11B shows weight of mice implanted with WU-386 cells. FIG. 11C shows weight of mice implanted with JH-2-002 cells. After 7-10 days, mice were treated daily with 1.5 mg/kg deucravacitinib (Deucra, BMS-986165), 30 mg/kg mirdametinib (Mirda), the combination of drugs, or vehicle control for three weeks or until tumors reached the maximum allowed volume. Mouse body weight, an indicator of health, was measured 2-3 times per week.

Figure 12A:
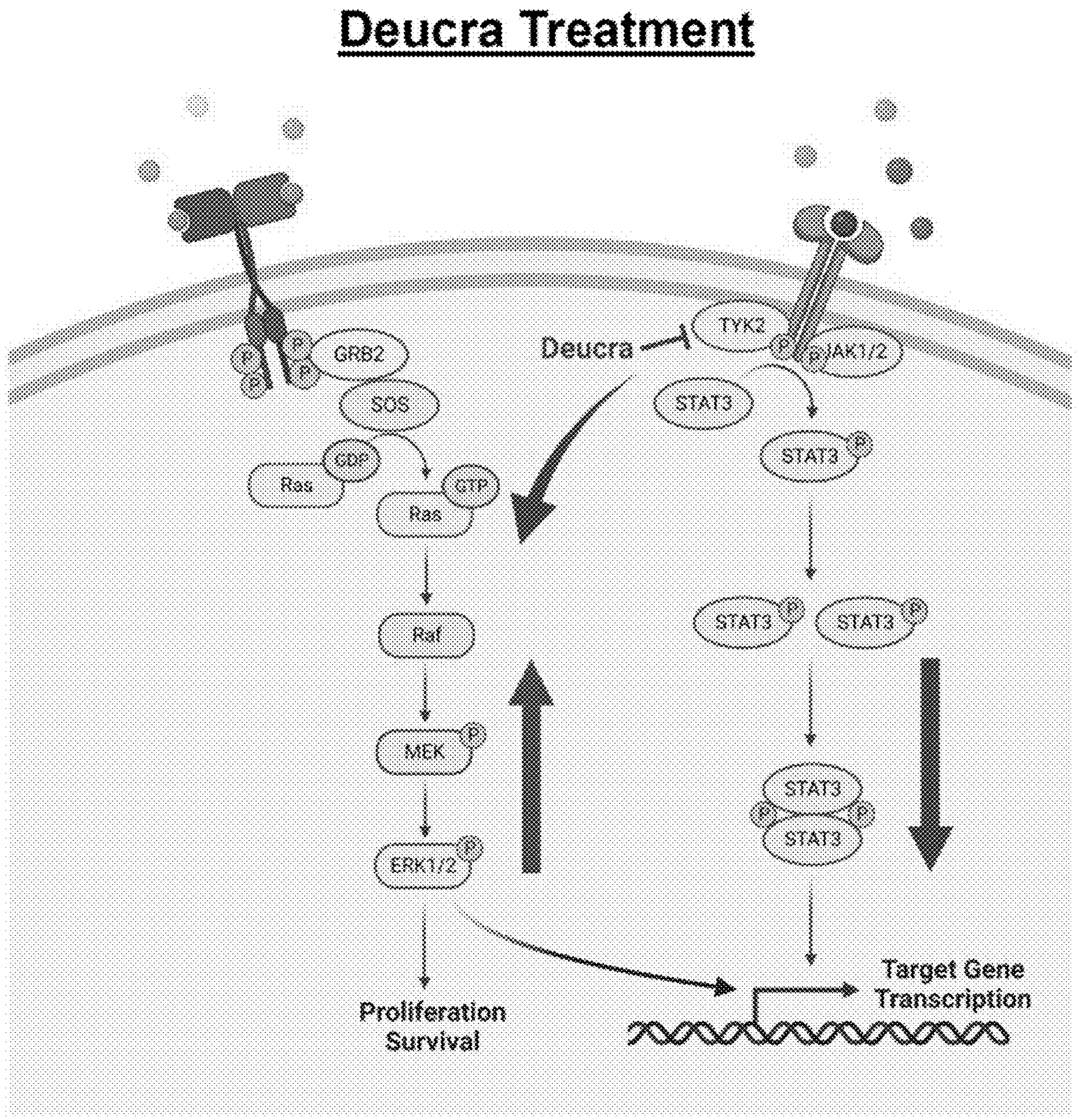
Figure 12B:
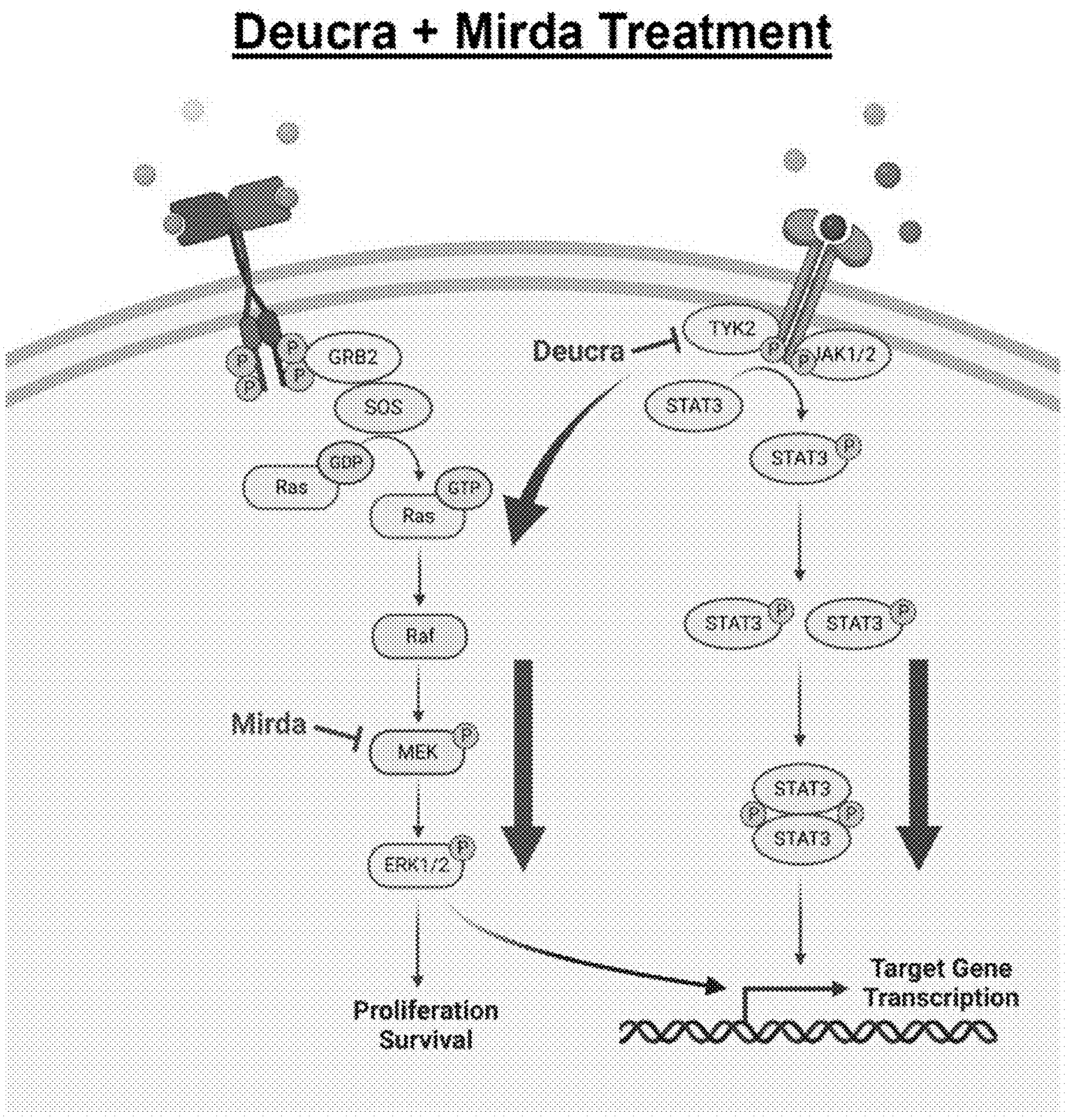

FIG. 12(A-B) is an exemplary embodiment showing the combination of drugs inhibiting TYK2 and MEK block MPNST tumor growth in mice in accordance with the present disclosure. FIG. 12A is a diagram showing TYK2/STAT3 and MEK/MAPK pathways after treatment with Deucra in MPNST cells. FIG. 12B is a diagram showing TYK2/STAT3 and MEK/MAPK pathways after treatment with Deucra and Mirda in MPNST cells.

Figure 13B:
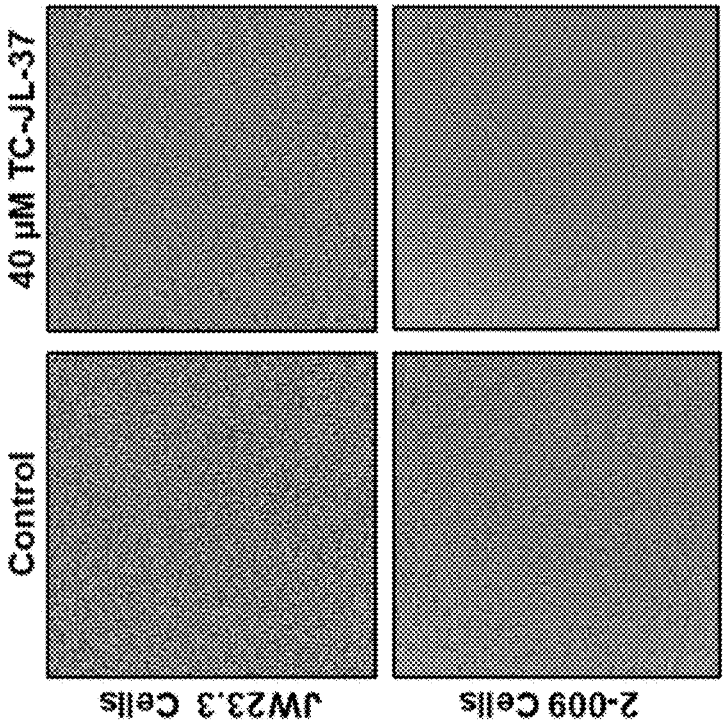
Figure 13A:
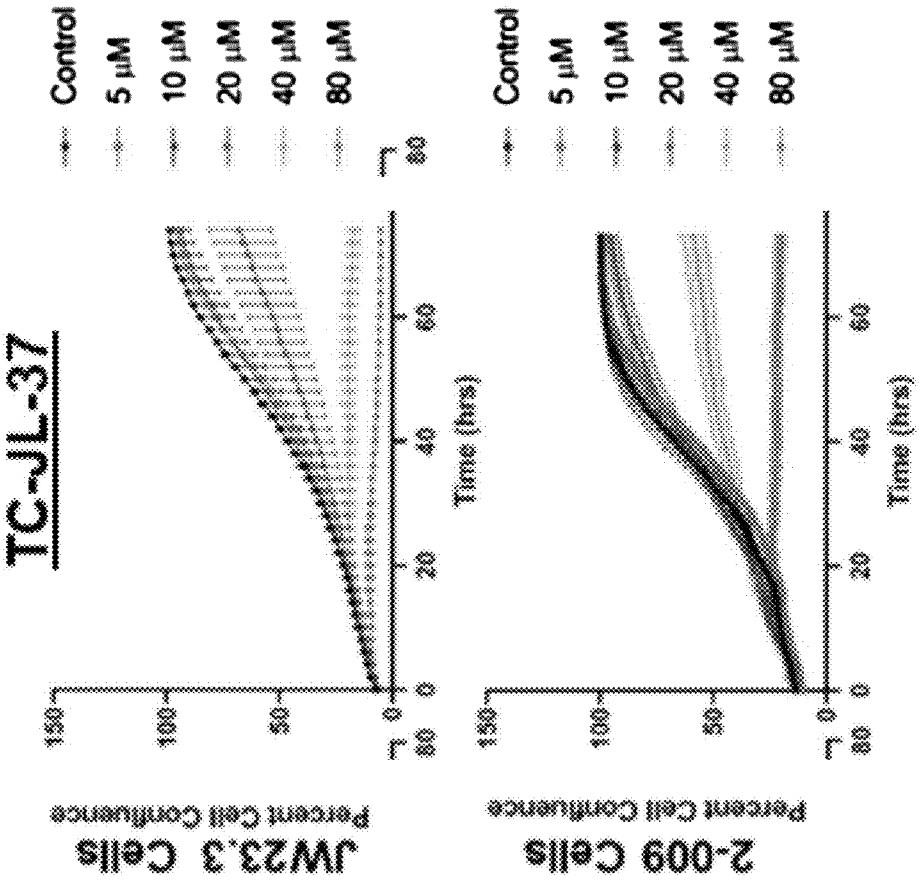

FIG. 13(A-B) is an exemplary embodiment showing TYK2 inhibitors reduce proliferation and induce apoptosis in MPNST cells in accordance with the present disclosure. FIG. 13A includes graphs showing confluence of JW23.3 and 2-009 cells treated with TYK2 inhibitor TC-JL-37 over 3 days. Cell confluence was determined by the IncuCyte live cell imaging assays. FIG. 13B includes representative images of IncuCyte assay at 72 hours, with YOYO-1 green fluorescence as an indicator of apoptosis.

Figure 14:
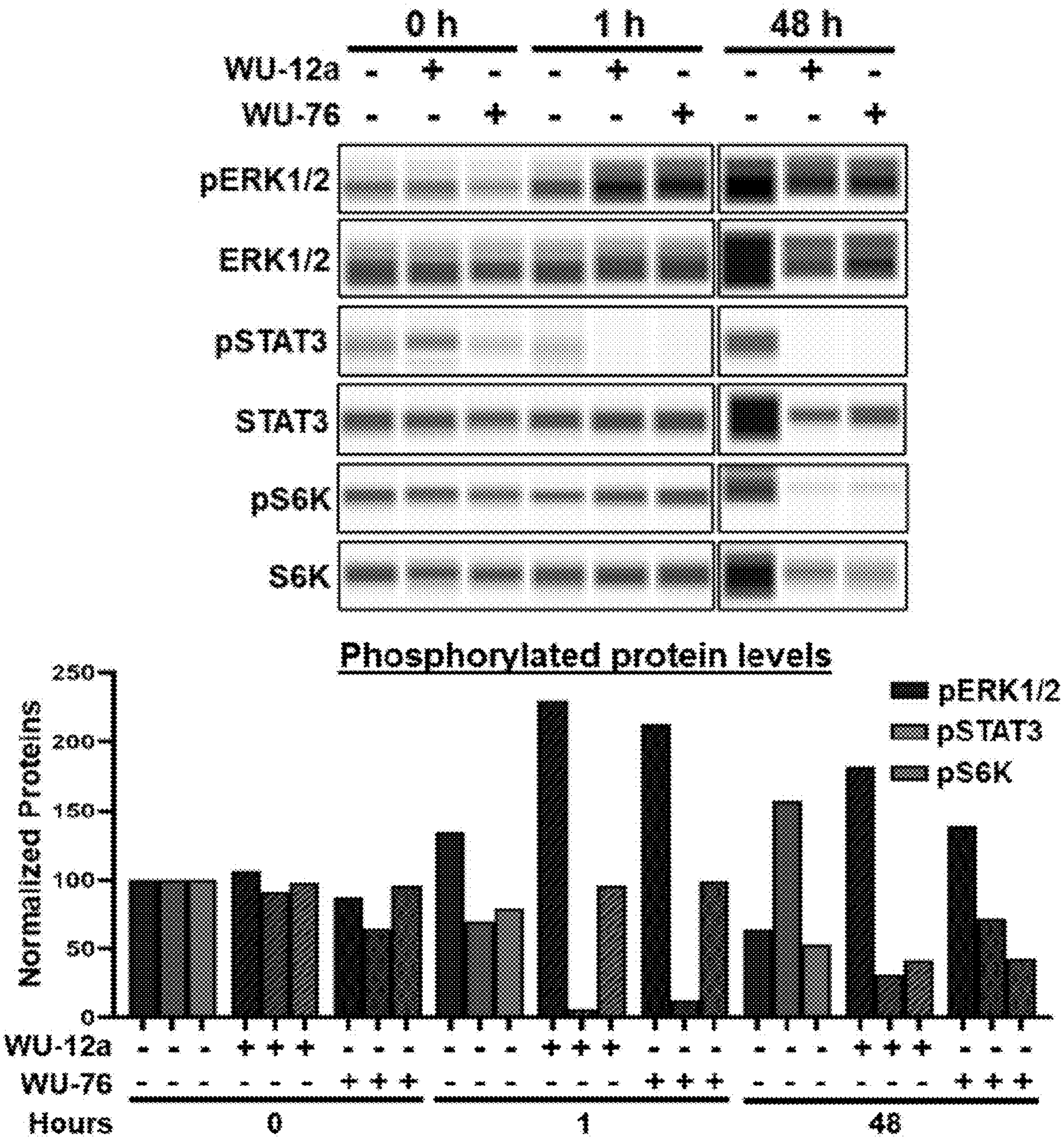

FIG. 14 contains images and graphs showing TYK2 inhibition leads to compensatory stimulation of the MEK/MAP kinase (MAPK) pathway in MPNST cells. JW23.3 cells were incubated with TYK2 inhibitors (40 μM WU-12 or WU-76), and protein levels were analyzed by WES western system.

Figure 15A:
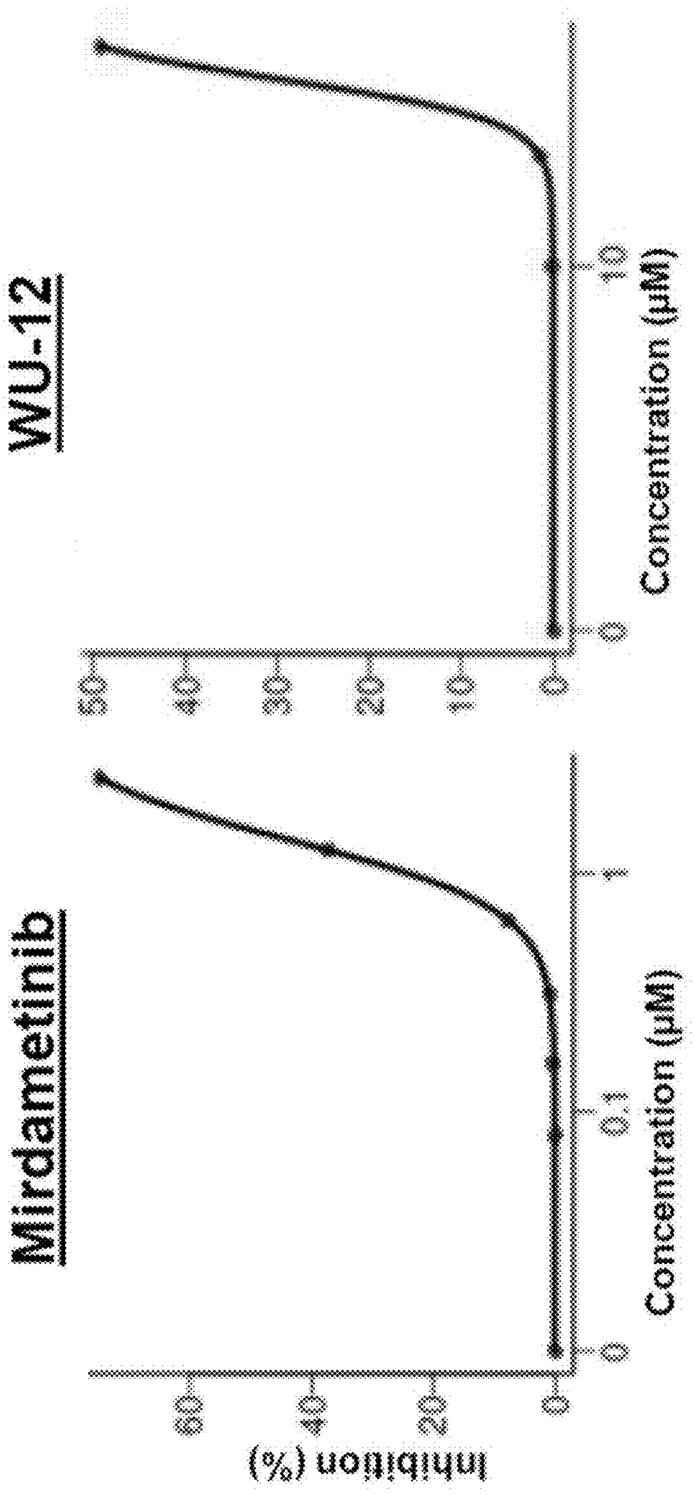
Figure 15B:
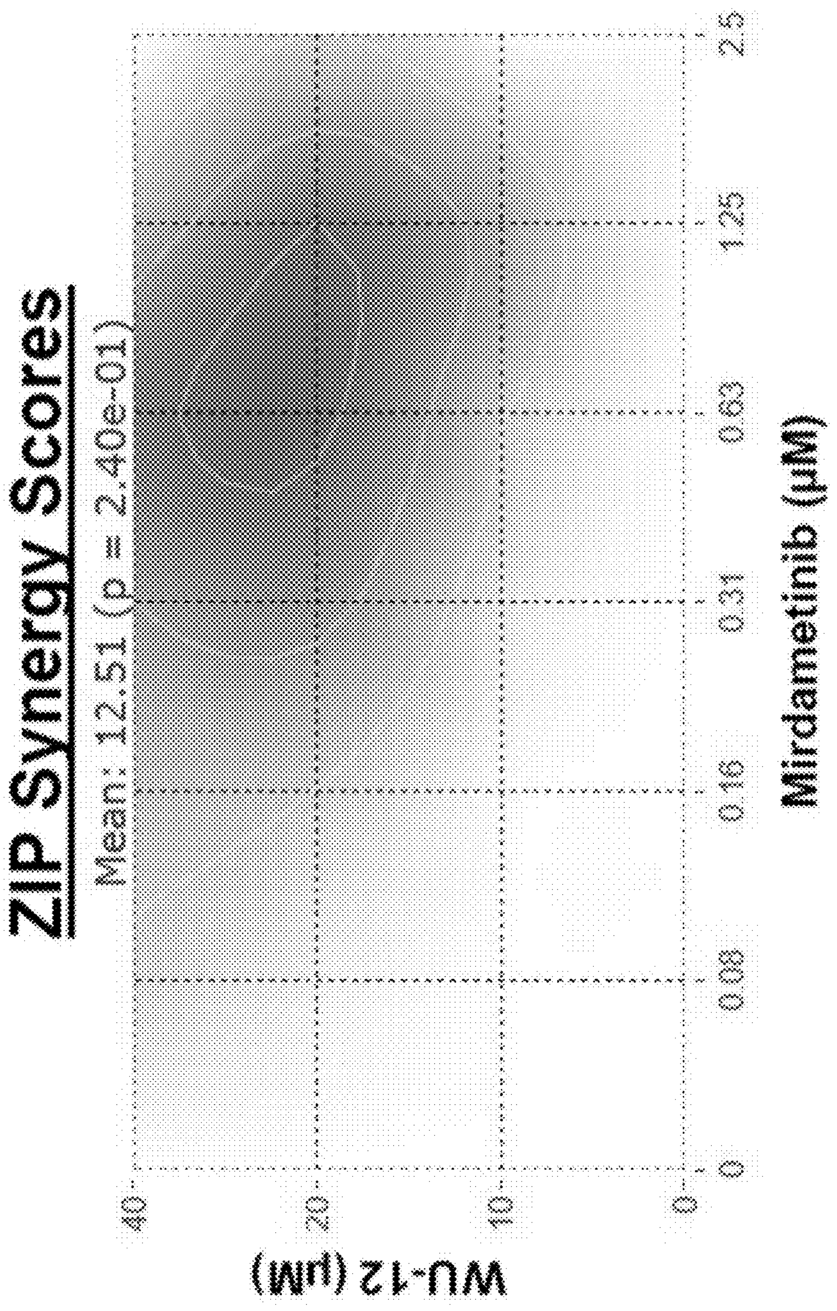

FIG. 15(A-B) is an exemplary embodiment showing inhibitors of TYK2 (WU-12) and MEK (mirdametinib) act synergistically to reduce proliferation in JW23.3 MPNST cells in accordance with the present disclosure. FIG. 15A contains graphs showing the percent inhibition dose response calculated for each drug alone. FIG. 15B is a heat map showing synergy analysis using the ZIP method. Cell confluence was analyzed by IncuCyte assay after 72-hour incubation with drugs.

Figure 16A:
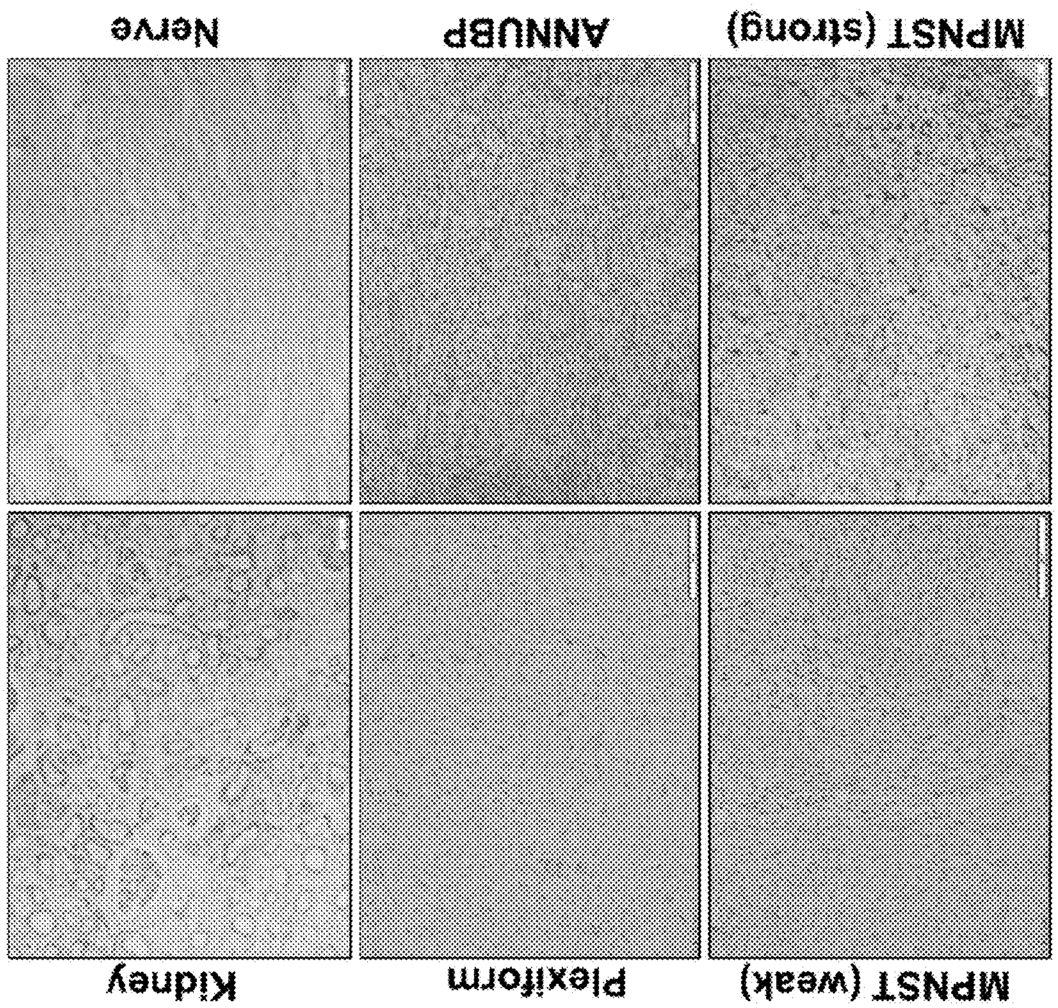
Figures 16B, 16C:
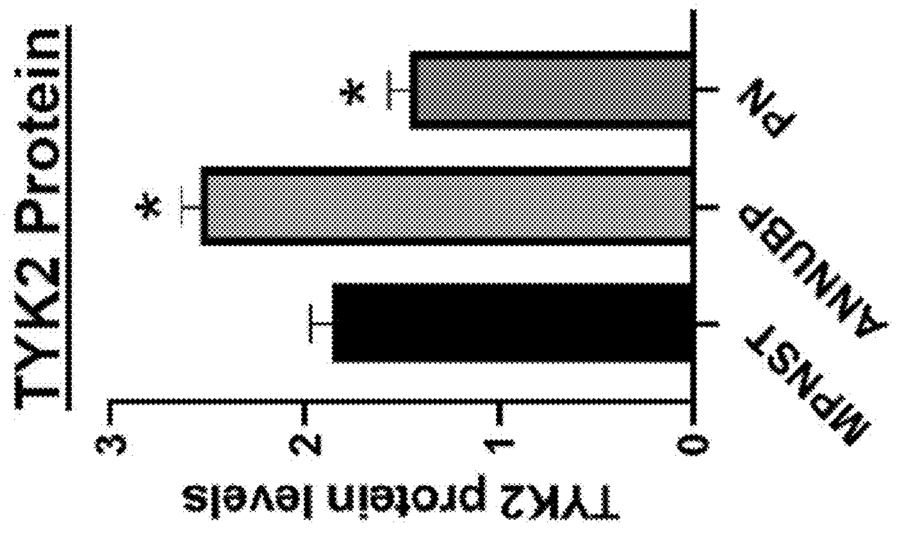

FIG. 16(A-C) is an exemplary embodiment showing TYK2 immunostaining in MPNST and precursor tumors in accordance with the present disclosure. FIG. 16A contains representative images of TYK2 staining in MPNST, PN, ANNUBP, kidney (positive control), and nerve (negative control). FIG. 16B is a bar graph showing TYK2 intensity scores for MPNST, PN, and ANNUBP samples ($p<0.5$). FIG. 16C is a table showing quantification of number of positive and negative/weak cases observed for each type of tumor.

DETAILED DESCRIPTION

The present disclosure is based, in part, on the discovery that the combination of a TYK2 inhibitor and MEK inhibitor synergistically inhibits proliferation and increases apoptosis of Malignant Peripheral Nerve Sheath Tumors (MPNSTs).

MPNSTs are aggressive sarcomas with dismal prognosis and there is an urgent need for more effective treatment strategies. It was previously found that Tyrosine Kinase 2 (TYK2) is overexpressed in the majority of MPNST. TYK2 and other JAKs mediate cytokine signaling thereby influencing inflammation, immune function, and cancer progression. Herein is demonstrated that drugs targeting TYK2 decrease proliferation and induce apoptosis in MPNST, while inhibiting STAT3 activation (see e.g., Example 1). TYK2 inhibitors also stimulate the MEK/MAP-kinase pathway, which may be a compensatory survival mechanism for MPNST. Addition of a MEK inhibitor, mirdametinib, synergizes with the TYK2 inhibitor, deucravacitinib, to block proliferation and promote apoptosis of MPNST both in vitro and in three different in vivo models (see e.g., Example 1). Thus, the combination of TYK2 inhibitors and MEK inhibitors, such as deucravacitinib and mirdametenib, is a promising therapy for cancers such as NF1-associated MPNSTs.

TYK2 and MEK Inhibiting Agents

One aspect of the present disclosure provides for targeting of TYK2 and MEK, its receptor, or its downstream signaling with TYK2 and MEK inhibiting agents in a combination therapy approach (which can be administered sequentially or simultaneously). The present disclosure provides methods of treating or preventing cancer based on the discovery that combination treatment with a TYK2 inhibitor (e.g., deucravacitinib) and a MEK inhibitor (e.g., mirdametinib) synergistically reduces proliferation and increases apoptosis of MPNST cells, and reduces tumor volume (see e.g., Example 1).

As described herein, inhibitors or antagonists of TYK2 and/or MEK (e.g., antibodies, fusion proteins, small molecules) can inhibit TYK2 and/or MEK, downregulate TYK2 and/or MEK, or knockdown TYK2 and/or MEK.

In some embodiments, the TYK2 and/or MEK inhibiting agent can inhibit TYK2 and/or MEK signaling.

In some embodiments, the TYK2 inhibiting agent is highly specific for TYK2 and does not inhibit other members of the Janus family of non-receptor tyrosine kinases, such as JAK1, JAK2, or JAK3. For example, the TYK2 inhibiting agent can be the specific TYK2 inhibitor deucravacitinib (BMS-986165) having a structure

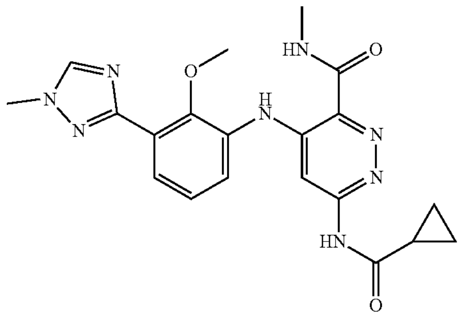 [SMILES: CNC(=O)c1nnc(NC(=O)C2CC2)cc1Nc1cccc(-c2ncn(C)n2)c1OC]

(or a pharmaceutically acceptable salt, solvate, polymorph, tautomer, prodrug, analog, or stereoisomer thereof or optionally substituted analog thereof). The specific TYK2 inhibitor deucravacitinib (BMS-986165) is FDA approved for plaque psoriasis. As another example, the TYK2 inhibiting agent can be compounds of Formula I or Formula II as described herein below (such as WU-12 or WU-76, respectively). As another example, the TYK2 inhibiting agent can be TC-JL-37 having a structure

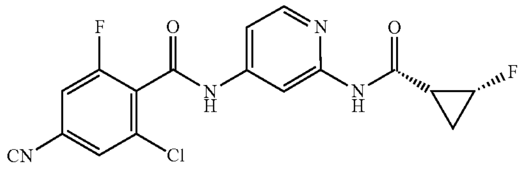

(or a pharmaceutically acceptable salt, solvate, polymorph, tautomer, prodrug, analog, or stereoisomer thereof or optionally substituted analog thereof). As yet another example, the TYK2 inhibitor can be PF-06826647.

In some embodiments, the TYK2 inhibiting agent may be a dual TYK2/JAK inhibitor, such as brepocitinib.

In some embodiments, the MEK inhibiting agent inhibits MEK1 and/or MEK2 and/or the MAPK/ERK pathway. For example, the MEK inhibiting agent can be mirdametinib (PD-0325901). As another example, the MEK inhibiting agent can be Binimetinib (MEK162), Cobimetinib or XL518, Selumetinib, Trametinib (GSK1120212), TAK-733, PD-325901, or CI-1040 (PD184352).

As another example, a TYK2 or MEK inhibiting agent can be an inhibitory protein that antagonizes TYK2 or MEK. For example, the TYK2 and/or MEK inhibiting agent can be a viral protein, which has been shown to antagonize TYK2 and/or MEK.

As another example, a TYK2 and/or MEK inhibiting agent can be a short hairpin RNA (shRNA) or a short interfering RNA (siRNA) targeting TYK2 and/or MEK.

As another example, a TYK2 and/or MEK inhibiting agent can be an sgRNA targeting TYK2 and/or MEK.

TYK2 and/or MEK Signal Reduction, Elimination, or Inhibition by Small Molecule Inhibitors, shRNA, siRNA, or ASOs As described herein, a TYK2 and/or MEK inhibiting agent can be used for use in cancer therapy. A TYK2 and/or MEK inhibiting agent can be used to reduce/eliminate TYK2 and/or MEK signals. For example, a TYK2 and/or MEK inhibiting agent can be a small molecule inhibitor of TYK2 and/or MEK. As another example, a TYK2 and/or MEK inhibiting agent can be a short hairpin RNA (shRNA).

As another example, a TYK2 and/or MEK inhibiting agent can be a short interfering RNA (siRNA).

As another example, RNA (e.g., long noncoding RNA (IncRNA)) can be targeted with antisense oligonucleotides (ASOs) as a therapeutic. Processes for making ASOs targeted to RNAs are well known; see e.g., Zhou et al. 2016 Methods Mol Biol. 1402:199-213. Except as otherwise noted herein, therefore, the process of the present disclosure can be carried out in accordance with such processes.

Inhibition of agents as described herein can be determined by standard pharmaceutical procedures in assays or cell cultures for determining the $IC_{50}$. The half maximal inhibitory concentration ($IC_{50}$) is a measure of the potency of a substance in inhibiting a specific biological or biochemical function. The $IC_{50}$ is a quantitative measure that indicates how much of a particular inhibitory substance (e.g., pharmaceutical agent or drug) is needed to inhibit, in vitro, a given biological process or biological component by 50%. The biological component could be an enzyme, cell, cell receptor, or microorganism, for example. $IC_{50}$ values are typically expressed as molar concentration. $IC_{50}$ is generally used as a measure of antagonist drug potency in pharmacological research. $IC_{50}$ is comparable to other measures of potency, such as ECK for excitatory drugs. ECK represents the dose or plasma concentration required for obtaining 50% of a maximum effect in vivo. $IC_{50}$ can be determined with functional assays or with competition binding assays.

Examples of TYK2 and/or MEK inhibiting agents are described herein. The MEK inhibiting agent can be, for example, mirdametinib and the TYK2 inhibiting agent can be, for example, deucravacitinib, a compound according to Formula I, below (e.g., WU-12), a compound according to Formula II, below (e.g., WU-76), TC-JL-37 (as shown herein above), or a pharmaceutically acceptable salt, solvate, polymorph, tautomer, prodrug, analog, or stereoisomer thereof or optionally substituted analog thereof.

Formula I

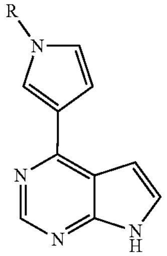

Formula II

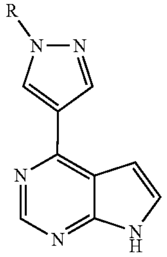

R (i.e., the R group) can be optionally substituted with one or more groups independently selected from the group consisting of hydroxyl; hydroxyl; amine; $C_{1-10}$carboxylic acid; $C_{1-10}$carboxyl, straight chain or branched $C_{1-10}$alkyl, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; hydroxyl; amine; $C_{1-10}$carboxyl, $C_{1-10}$carboxylic acid; $C_{1-10}$carboxyl, straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; heterocyclyl; straight chain or branched $C_{1-10}$alkyl amine; heterocyclic amine; aryl comprising a phenyl; heteroaryl containing from 1 to 4 N, O, or S atoms; and pyrrol, pyrrolo, pyrimidin, cyanospiro, heptan, pyrazol, carbamoyl, and/or alkane sulfonamide(s). Any of the above can be further optionally substituted.

According to the present disclosure, a TYK2 inhibiting agent can be, for example, a compound according to Formula I. The TYK2 inhibiting agent WU-12 disclosed herein has a structure according to Formula I wherein R comprises an ethanesulfonamide. The TYK2 inhibiting agent WU-76 disclosed herein has a structure according to Formula II wherein the R group comprises an ethanesulfonamide.

The term "imine" or "imino", as used herein, unless otherwise indicated, can include a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, can include —OH. The "hydroxyl" can be optionally substituted.

The terms "halogen" and "halo", as used herein, unless otherwise indicated, include a chlorine, chloro, Cl; fluorine, fluoro, F; bromine, bromo, Br; or iodine, iodo, or I.

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of aryl groups include, but are not limited to, phenyl, benzyl, naphthyl, or anthracenyl. The "aryl" can be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, can include saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_{1-10}$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, or -3-methyl-1 butynyl. An alkyl can be saturated, partially saturated, or unsaturated. The "alkyl" can be optionally substituted.

The term "carboxyl", as used herein, unless otherwise indicated, can include a functional group consisting of a carbon atom double bonded to an oxygen atom and single bonded to a hydroxyl group (—COOH). The "carboxyl" can be optionally substituted.

The term "carbonyl", as used herein, unless otherwise indicated, can include a functional group consisting of a carbon atom double-bonded to an oxygen atom (C═O). The "carbonyl" can be optionally substituted.

The term "alkenyl", as used herein, unless otherwise indicated, can include alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, can include alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, can include a functional group derived from an aliphatic carboxylic acid, by removal of the hydroxyl (—OH) group. The "acyl" can be optionally substituted.

The term "alkoxyl", as used herein, unless otherwise indicated, can include O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-m ethylbutyl, —O-2-methyl pentyl, —O-3-methyl pentyl, —O-2,2-dimethyl butyl, —O-2,3-di methylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2, 4dimethylpentyl, —O-2-methylheptyl, —O-3-methylheptyl, —O-vinyl, —O-allyl, —O-1-butenyl, —O-2-butenyl, —O— isobutylenyl, —O-1-pentenyl, —O-2-pentenyl, —O-3-methyl-1-butenyl, —O-2-methyl-2-butenyl, —O-2, 3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O— cyclohexyl, —O-cycloheptyl, —O-cyclooctyl, —O-cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, $(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl, or —O—$(CH_2)_2$-cyclodecyl. An alkoxyl can be saturated, partially saturated, or unsaturated. The "alkoxyl" can be optionally substituted.

The term "cycloalkyl", as used herein, unless otherwise indicated, can include an aromatic, a non-aromatic, saturated, partially saturated, or unsaturated, monocyclic or fused, spiro or unfused bicyclic or tricyclic hydrocarbon referred to herein containing a total of from 1 to 10 carbon atoms (e.g., 1 or 2 carbon atoms if there are other heteroatoms in the ring), preferably 3 to 8 ring carbon atoms. Examples of cycloalkyls include, but are not limited to, 03-10 cycloalkyl groups include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. The term "cycloalkyl" also can include -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl, or —$CH_2$-cyclooctyl. The "cycloalkyl" can be optionally substituted. A "cycloheteroalkyl", as used herein, unless otherwise indicated, can include any of the above with a carbon substituted with a heteroatom (e.g., O, S, N).

The term "heterocyclic" or "heteroaryl", as used herein, unless otherwise indicated, can include an aromatic or non-aromatic cycloalkyl in which one to four of the ring carbon atoms are independently replaced with a heteroatom from the group consisting of O, S, and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "heterocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, can include a —CN group. The "cyano" can be optionally substituted.

The term "alcohol", as used herein, unless otherwise indicated, can include a compound in which the hydroxyl functional group (—OH) is bound to a carbon atom. In particular, this carbon center should be saturated, having single bonds to three other atoms. The "alcohol" can be optionally substituted.

The term "solvate" is intended to mean a solvate form of a specified compound that retains the effectiveness of such compound. Examples of solvates include compounds of the invention in combination with, for example, water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "μg", as used herein, is intended to mean micrograms. The term "h", as used herein, is intended to mean hour. The term "min", as used herein, is intended to mean minute. The term "M", as used herein, is intended to mean molar. The term "μL", as used herein, is intended to mean microliter. The term "μM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HPLC", as used herein, is intended to mean high performance liquid chromatograph. The term "RT", as used herein, is intended to mean room temperature. The term "e.g.,", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion, or another counterion. The counterion may be any organic or inorganic moiety that stabilizes the charge on the parent compound. Furthermore, a pharmaceutically acceptable salt may have more than one charged atom in its structure. In instances where multiple charged atoms are part of the pharmaceutically acceptable salt, the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further can include a stoichiometric or non-stoichiometric amount of water bound by non-covalent intermolecular forces.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The term "transfection," as used herein, refers to the process of introducing nucleic acids into cells by non-viral methods. The term "transduction," as used herein, refers to the process whereby foreign DNA is introduced into another cell via a viral vector.

The terms "heterologous DNA sequence", "exogenous DNA segment", or "heterologous nucleic acid," as used herein, each refers to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

An "expression vector", otherwise known as an "expression construct", is generally a plasmid or virus designed for gene expression in cells. The vector is used to introduce a specific gene into a target cell and can commandeer the cell's mechanism for protein synthesis to produce the protein encoded by the gene. Expression vectors are the basic tools in biotechnology for the production of proteins. The vector is engineered to contain regulatory sequences that act as enhancer and/or promoter regions and lead to efficient transcription of the gene carried on the expression vector. The goal of a well-designed expression vector is the efficient production of protein, and this may be achieved by the production of significant amount of stable messenger RNA, which can then be translated into protein. The expression of a protein may be tightly controlled, and the protein is only produced in significant quantity, when necessary, through the use of an inducer, in some systems however the protein may be expressed constitutively. As described herein, *Escherichia coli* is used as the host for protein production, but other cell types may also be used.

In molecular biology, an "inducer" is a molecule that regulates gene expression. An inducer can function in two ways, such as:

(i) By disabling repressors. The gene is expressed because an inducer binds to the repressor. The binding of the inducer to the repressor prevents the repressor from binding to the operator. RNA polymerase can then begin to transcribe operon genes.

(ii) By binding to activators. Activators generally bind poorly to activator DNA sequences unless an inducer is present. An activator binds to an inducer and the complex binds to the activation sequence and activates target gene. Removing the inducer stops transcription. Because a small inducer molecule is required, the increased expression of the target gene is called induction.

Repressor proteins bind to the DNA strand and prevent RNA polymerase from being able to attach to the DNA and synthesize mRNA. Inducers bind to repressors, causing them to change shape and preventing them from binding to DNA. Therefore, they allow transcription, and thus gene expression, to take place.

For a gene to be expressed, its DNA sequence must be copied (in a process known as transcription) to make a smaller, mobile molecule called messenger RNA (mRNA), which carries the instructions for making a protein to the site where the protein is manufactured (in a process known as translation). Many different types of proteins can affect the level of gene expression by promoting or preventing transcription. In prokaryotes (such as bacteria), these proteins often act on a portion of DNA known as the operator at the beginning of the gene. The promoter is where RNA polymerase, the enzyme that copies the genetic sequence and synthesizes the mRNA, attaches to the DNA strand.

Some genes are modulated by activators, which have the opposite effect on gene expression as repressors. Inducers can also bind to activator proteins, allowing them to bind to the operator DNA where they promote RNA transcription. Ligands that bind to deactivate activator proteins are not, in the technical sense, classified as inducers, since they have the effect of preventing transcription.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "ribosome binding site", or "ribosomal binding site (RBS)", refers to a sequence of nucleotides upstream of the start codon of an mRNA transcript that is responsible for the recruitment of a ribosome during the initiation of translation. Generally, RBS refers to bacterial sequences, although internal ribosome entry sites (IRES) have been described in mRNAs of eukaryotic cells or viruses that infect eukaryotes. Ribosome recruitment in eukaryotes is generally mediated by the 5' cap present on eukaryotic mRNAs.

A "transcribable nucleic acid molecule" as used herein refers to any nucleic acid molecule capable of being transcribed into an RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal, or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above-required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2, or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A. For example, the percent identity can be at least 80% or about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

Substitution refers to the replacement of one amino acid with another amino acid in a protein or the replacement of one nucleotide with another in DNA or RNA. Insertion refers to the insertion of one or more amino acids in a protein or the insertion of one or more nucleotides with another in DNA or RNA. Deletion refers to the deletion of one or more amino acids in a protein or the deletion of one or more nucleotides with another in DNA or RNA. Generally, substitutions, insertions, or deletions can be made at any position so long as the required activity is retained.

So-called conservative exchanges can be carried out in which the amino acid which is replaced has a similar property as the original amino acid, for example, the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine), hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. An amino acid sequence can be modulated with the help of art-known computer simulation programs that can produce a polypeptide with, for example, improved activity or altered regulation. On the basis of these artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[$Na^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transformed cells can be selected and propagated to provide recombinant host cells that comprise the expression vector stably integrated in the host cell genome.

Conservative Substitutions I

| Side Chain Characteristic | Amino Acid |
|---|---|
| Aliphatic Non-polar | G A P I L V |
| Polar-uncharged | C S T M N Q |
| Polar-charged | D E K R |

-continued

| Conservative Substitutions I | |
|---|---|
| Side Chain Characteristic | Amino Acid |
| Aromatic | H F W Y |
| Other | N Q D E |

| Conservative Substitutions II | |
|---|---|
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids that may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Genome Editing

As described herein, TYK2 and/or MEK inhibiting agent signals can be modulated (e.g., reduced, eliminated, or enhanced) using genome editing. Processes for genome editing are well known; see e.g., Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of TYK2 and/or MEK inhibiting agent by genome editing can result in protection from proliferative diseases, disorders, or conditions, such as cancer.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for cancer treatment or prevention to target cells by the removal or addition of TYK2 and/or MEK signals (e.g., activate (e.g., CRISPRa), upregulate, overexpress, downregulate TYK2 and/or MEK).

For example, the methods as described herein can comprise a method for altering a target polynucleotide sequence in a cell comprising contacting the polynucleotide sequence with a clustered regularly interspaced short palindromic repeats-associated (Cas) protein.

Gene Therapy and Genome Editing

Gene therapies can include inserting a functional gene with a viral vector. Gene therapies for cancer are rapidly advancing.

There has recently been an improved landscape for gene therapies. For example, in the first quarter of 2019, there were 372 ongoing gene therapy clinical trials (*Alliance for Regenerative Medicine,* 5/9/19).

Any vector known in the art can be used. For example, the vector can be a viral vector selected from retrovirus, lentivirus, herpes, adenovirus, adeno-associated virus (AAV), rabies, Ebola, lentivirus, or hybrids thereof.

Gene Therapy Strategies.

| | Strategy | Associated experimental models |
|---|---|---|
| | Viral Vectors | |
| Retroviruses | Retroviruses are RNA viruses transcribing their single-stranded genome into a double-stranded DNA copy, which can integrate into host chromosome | Murine model of MPS VII<br>Canine model of MPS VII |
| Adenoviruses (Ad) | Ad can transfect a variety of quiescent and proliferating cell types from various species and can mediate robust gene expression | Murine model of Pompe, Fabry, Walman diseases, aspartylglucosaminuria and MPS VII |
| Adeno-associated Viruses (AAV) | Recombinant AAV vectors contain no viral DNA and can carry ~4.7 kb of foreign transgenic material. They are replication defective and can replicate only while coinfecting with a helper virus | Murine models of Pompe, Fabry diseases, Aspartylglucosaminuria, Krabbe disease, Metachromatic leukodystrophy, MPS 1, MPSII, MPSIIIA, MPSIIIB, MPSIV, MPSVI, MPS VII, CLN1, CLN2, CLN3, CLN5, CLN6 |
| | Non-viral vectors | |
| plasmid DNA (pDNA) | pDNA has many desired characteristics as a gene therapy vector; there are no limits on the size or genetic constitution of DNA, it is relatively inexpensive to supply, and unlike viruses, antibodies are not generated against DNA in normal individuals | Mouse model of Fabry disease |
| RNAi | RNAi is a powerful tool for gene specific silencing that could be useful as an enzyme reduction therapy or means to promote read-through of a premature stop codon | Transgenic mouse strain<br>Mouse models of acute liver failure<br>Mice with hepatitis B virus<br>Fabry mouse |

Gene therapy can allow for the constant delivery of the enzyme directly to target organs and eliminates the need for weekly infusions. Also, correction of a few cells could lead to the enzyme being secreted into the circulation and taken up by their neighboring cells (cross-correction), resulting in widespread correction of the biochemical defects. As such, the number of cells that must be modified with a gene transfer vector is relatively low.

Genetic modification can be performed either ex vivo or in vivo. The ex vivo strategy is based on the modification of cells in culture and transplantation of the modified cell into a patient. Cells that are most commonly considered therapeutic targets for monogenic diseases are stem cells. Advances in the collection and isolation of these cells from a variety of sources have promoted autologous gene therapy as a viable option.

The use of endonucleases for targeted genome editing can solve the limitations presented by the usual gene therapy protocols. These enzymes are custom molecular scissors, allowing cutting DNA into well-defined, perfectly specified pieces, in virtually all cell types. Moreover, they can be delivered to the cells by plasmids that transiently express the nucleases, or by transcribed RNA, avoiding the use of viruses.

Cancer

Methods and compositions as described herein can be used for the prevention, treatment, or slowing the progression of a proliferative disease, disorder, or condition, such as cancer or tumor growth.

For example, the proliferative disease disorder, or condition can be neurofibromatosis Type 1 (NF1) cancer predisposition syndrome, benign plexiform neurofibromas (PN), malignant peripheral nerve sheath tumor (MPNST), or ANNUBP (atypical neurofibromatous neoplasms of uncertain biologic potential or atypical neurofibromas)

MPNSTs are aggressive sarcomas that often arise in people with Neurofibromatosis Type I (NF1), the most common cancer predisposition syndrome. Individuals with NF1 have one mutated copy of the NF1 gene, increasing the risk of developing benign plexiform neurofibromas (PN), which can later undergo malignant transformation to MPNST. These individuals may also develop ANNUBP, which refers to neurofibromas with atypical histological features that are considered to be premalignant with an increased risk of progressing to a MPNST. In addition to NF1, the genes encoding CDKN2A, TP53, EED, and SUZ12 are frequently altered in MPNST.

In some embodiments, the proliferative disease disorder, or condition may be a tumor or cancer such as an MPNST comprising an activating mutation in tyrosine kinase 2 (TYK2). For example, the activating mutation may be a mutation comprised in the conserved Jak1 homology domain (KH2) of TYK2, such as Pro1104Ala. A tumor or cancer such as MPNST comprising an activating mutation in TYK2 may be particularly responsive to the TYK2 inhibitor and MEK inhibitor combination therapy of the present disclosure. The TYK2 mutation may be identified, for example, by any of known methods in the art, such as genomic screening or next generation sequencing.

In some embodiments, the proliferative disease disorder, or condition may be a tumor or cancer such as an MPNST that overexpresses TYK2 (with or without a TYK2 mutation). “Overexpress” is used to mean that the tumor or cancer such as an MPNST exhibits higher expression of TYK2 gene or protein product compared to a control. The control may be, for example, cells from a healthy subject or from benign PNs. Overexpression of TYK2 may be detected by any means known in the art, such as microarray, qPCR, or immunohistochemistry.

As another example, the cancer can be Acute Lymphoblastic Leukemia (ALL); Acute Myeloid Leukemia (AML); Adrenocortical Carcinoma; AIDS-Related Cancers; Kaposi Sarcoma (Soft Tissue Sarcoma); AIDS-Related Lymphoma (Lymphoma); Primary CNS Lymphoma (Lymphoma); Anal Cancer; Appendix Cancer; Gastrointestinal Carcinoid Tumors; Astrocytomas; Atypical Teratoid/Rhabdoid Tumor, Childhood, Central Nervous System (Brain Cancer); Basal Cell Carcinoma of the Skin; Bile Duct Cancer; Bladder Cancer; Bone Cancer (including Ewing Sarcoma and Osteosarcoma and Malignant Fibrous Histiocytoma); Brain Tumors; Breast Cancer; Bronchial Tumors; Burkitt Lymphoma; Carcinoid Tumor (Gastrointestinal); Childhood Carcinoid Tumors; Cardiac (Heart) Tumors; Central Nervous System cancer; Atypical Teratoid/Rhabdoid Tumor, Childhood (Brain Cancer); Embryonal Tumors, Childhood (Brain Cancer); Germ Cell Tumor, Childhood (Brain Cancer); Primary CNS Lymphoma; Cervical Cancer; Cholangiocarcinoma; Bile Duct Cancer Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell; Ductal Carcinoma In Situ (DCIS); Embryonal Tumors, Central Nervous System, Childhood (Brain Cancer); Endometrial Cancer (Uterine Cancer); Ependymoma, Childhood (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Intraocular Melanoma; Retinoblastoma; Fallopian Tube Cancer; Fibrous Histiocytoma of Bone, Malignant, or Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors; Hepatocellular (Liver) Cancer; Histiocytosis, Langerhans Cell; Hodgkin Lymphoma; Hypopharyngeal Cancer; Intraocular Melanoma; Islet Cell Tumors; Pancreatic Neuroendocrine Tumors; Kaposi Sarcoma (Soft Tissue Sarcoma); Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Lymphoma; Male Breast Cancer; Malignant Fibrous Histiocytoma of Bone or Osteosarcoma; Melanoma; Melanoma, Intraocular (Eye); Merkel Cell Carcinoma (Skin Cancer); Mesothelioma, Malignant; Metastatic Cancer; Metastatic Squamous Neck Cancer with Occult Primary; Midline Tract Carcinoma Involving NUT Gene; Mouth Cancer; Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip or Oral Cavity Cancer; Oropharyngeal Cancer; Osteosarcoma and Malignant Fibrous Histiocytoma of Bone; Ovarian Cancer Pancreatic Cancer; Pancreatic Neuroendocrine Tumors (Islet Cell Tumors); Papillomatosis; Paraganglioma; Paranasal Sinus and Nasal Cavity Cancer; Parathyroid Cancer; Penile Cancer; Pharyngeal Cancer; Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer Renal Cell (Kidney) Cancer; Retinoblastoma; Rhabdomyosarcoma, Childhood (Soft Tissue Sarcoma); Salivary Gland Cancer; Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Uterine Sarcoma; Sezary Syndrome (Lymphoma); Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; T-Cell Lymphoma, Cutaneous; Lymphoma; Mycosis Fungoides and Sezary Syndrome; Testicular Cancer; Throat Cancer; Nasopharyngeal Cancer; Oropharyngeal Cancer; Hypopharyngeal Cancer; Thymoma and Thymic Carcinoma; Thyroid Cancer; Thyroid Tumors; Transitional Cell Cancer of the Renal Pelvis and Ureter (Kidney (Renal Cell) Cancer); Ureter and Renal Pelvis; Transitional Cell Cancer (Kidney (Renal Cell) Cancer; Urethral Cancer; Uterine Cancer, Endometrial; Uterine Sarcoma; Vaginal Cancer; Vascular Tumors (Soft Tissue Sarcoma); Vulvar Cancer; or Wilms Tumor. Brain or spinal cord tumors can be acoustic neuroma; astrocytoma, atypical teratoid rhabdoid tumor (ATRT); brain stem glioma; chordoma; chondrosarcoma; choroid plexus; CNS lymphoma; craniopharyngioma; cysts; ependymoma; ganglioglioma; germ cell tumor; glioblastoma (GBM); glioma; hemangioma; juvenile pilocytic astrocytoma (JPA); lipoma; lymphoma; medulloblastoma; meningioma; metastatic brain tumor; neurilemmomas; neurofibroma; neuronal & mixed neuronal-glial tumors; oligoastrocytoma; oligodendroglioma; optic nerve glioma; pineal tumor; pituitary tumor; primitive neuroectodermal (PNET); rhabdoid tumor; or schwannoma. An astrocytoma can be grade I pilocytic astrocytoma, grade II—low-grade astrocytoma, grade III anaplastic astrocytoma, or grade IV glioblastoma (GBM), or a juvenile pilocytic astrocytoma. A glioma can be a brain stem glioma, ependymoma, mixed glioma, optic nerve glioma, or subependymoma.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing a proliferative disease, disorder, or condition, such as cancer in a subject (e.g., a subject having cancer or at risk for cancer) in need of administration of a therapeutically effective amount of a TYK2 and/or MEK inhibiting agent, so as to inhibit TYK2 and MEK.

Methods described herein are generally performed on a subject in need thereof. A subject in need of the therapeutic methods described herein can be a subject having, diagnosed with, suspected of having, or at risk for developing a proliferative disease, disorder, or condition. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a TYK2 and/or MEK inhibiting agent is, for example, an amount that would cause the desired therapeutic effect in a subject while minimizing undesired side effects. In various embodiments, an effective amount of a TYK2 and/or MEK inhibiting agent described herein can substantially inhibit a proliferative disease, disorder, or condition, slow the progress of a proliferative disease, disorder, or condition, or limit the development of a proliferative disease, disorder, or condition.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a TYK2 and/or MEK inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit a proliferative disease, disorder, or condition, slow the progress of a proliferative disease, disorder, or condition, or limit the development of a proliferative disease, disorder, or condition.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a TYK2 and/or MEK inhibiting agent can occur as a single event or over a time course of treatment. For example, a TYK2 and/or MEK inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for a proliferative disease, disorder, or condition.

A TYK2 and/or MEK inhibiting agent can be administered simultaneously or sequentially with another agent, such as an antibiotic, an anti-inflammatory, or another agent. For example, a TYK2 and/or MEK inhibiting agent can be administered simultaneously with each other or another agent, such as an antibiotic or an anti-inflammatory. Simultaneous administration can occur through administration of separate compositions, each containing one or more of a TYK2 and/or MEK inhibiting agent, an antibiotic, an anti-inflammatory, or another agent. Simultaneous administration can occur through administration of one composition containing two or more of a TYK2 and/or MEK inhibiting agent, an antibiotic, an anti-inflammatory, or another agent. A TYK2 and/or MEK inhibiting agent can be administered sequentially with an antibiotic, an anti-inflammatory, or another agent. For example, a TYK2 and/or MEK inhibiting agent can be administered before or after administration of an antibiotic, an anti-inflammatory, or another agent.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general, a human equivalent dose (HED) in mg/kg can be calculated in accordance with the following formula (see e.g., Reagan-Shaw et al., *FASEB J.,* 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment, and the potency, stability, and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the TYK2 and/or MEK inhibiting agent may be administered in an amount from about 1 mg/kg to about 100 mg/kg, or about 1 mg/kg to about 50 mg/kg, or about 1 mg/kg to about 25 mg/kg, or about 1 mg/kg to about 15 mg/kg, or about 1 mg/kg to about 10 mg/kg, or about 1 mg/kg to about 5 mg/kg, or about 3 mg/kg. In some embodiments, a TYK2 and/or MEK inhibiting agent such as the MEK inhibiting agent, mirdametinib or TYK2 inhibiting agent, WU-12, WU-76, or TC-JL-37 may be administered in a range of about 1 mg/kg to about 200 mg/kg, or about 50 mg/kg to about 200 mg/kg, or about 50 mg/kg to about 100 mg/kg, or about 75 mg/kg to about 100 mg/kg, or about 100 mg/kg.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Cell Therapy

Cells generated according to the methods described herein can be used in cell therapy. Cell therapy (also called cellular therapy, cell transplantation, or cytotherapy) can be a therapy in which viable cells are injected, grafted, or implanted into a patient in order to effectuate a medicinal effect or therapeutic benefit. For example, transplanting T-cells capable of fighting cancer cells via cell-mediated immunity can be used in the course of immunotherapy, grafting stem cells can be used to regenerate diseased tissues, or transplanting beta cells can be used to treat diabetes.

Stem cell and cell transplantation has gained significant interest by researchers as a potential new therapeutic strategy for a wide range of diseases, in particular for degenerative and immunogenic pathologies.

Allogeneic cell therapy or allogenic transplantation uses donor cells from a different subject than the recipient of the cells. A benefit of an allogeneic strategy is that unmatched allogenic cell therapies can form the basis of "off the shelf" products.

Autologous cell therapy or autologous transplantation uses cells that are derived from the subject's own tissues. It could also involve the isolation of matured cells from diseased tissues, to be later re-implanted at the same or neighboring tissues. A benefit of an autologous strategy is that there is limited concern for immunogenic responses or transplant rejection.

Xenogeneic cell therapies or xenotransplantation uses cells from another species. For example, pig derived cells can be transplanted into humans. Xenogeneic cell therapies can involve human cell transplantation into experimental animal models for assessment of efficacy and safety or enable xenogeneic strategies to humans as well.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve taste of the product; or improve shelf life of the product.

Screening

Also provided are screening methods.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict the bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to, TYK2 and/or MEK inhibiting agents and assays for detecting TYK2 expression or mutations. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet web site specified by the manufacturer or distributor of the kit.

A control sample or a reference sample as described herein can be a sample from a healthy subject or sample, a wild-type subject or sample, or from populations thereof. A reference value can be used in place of a control or reference sample, which was previously obtained from a healthy subject or a group of healthy subjects or a wild-type subject or sample. A control sample or a reference sample can also be a sample with a known amount of a detectable compound or a spiked sample.

The methods and algorithms of the invention may be enclosed in a controller or processor. Furthermore, methods and algorithms of the present invention, can be embodied as a computer-implemented method or methods for performing such computer-implemented method or methods, and can also be embodied in the form of a tangible or non-transitory computer-readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general-purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: MEK Inhibition Synergizes with TYK2 Inhibitors in NF1-Associated Malignant Peripheral Nerve Sheath Tumors This Example describes the use of combination therapy TYK2 and MEK inhibitors to inhibit malignant peripheral nerve sheath tumors.

Malignant peripheral nerve sheath tumors (MPNST) are aggressive sarcomas with limited treatment options and poor survival rates. About half of MPNST cases are associated with the Neurofibromatosis Type 1 (NF1) cancer predisposition syndrome. Overexpression of TYK2 occurs in the majority of MPNST, implicating TYK2 as a therapeutic target.

Herein, the effects of pharmacologic TYK2 inhibition on MPNST cell proliferation and survival were examined using IncuCyte live cell assays in vitro, and downstream actions were analyzed using RNAseq, qPCR arrays, and validation of protein changes with the WES automated western system. Inhibition of TYK2 alone and in combination with MEK inhibition was evaluated in vivo with several patient derived MPNST cell lines.

Pharmacologic inhibition of TYK2 dose-dependently decreased proliferation and induced apoptosis over time. RNAseq pathway analysis on TYK2 inhibitor treated MPNST demonstrated decreased expression of cell cycle, mitotic, and glycolysis pathways. TYK2 inhibition resulted in MEK/MAP-kinase pathway gene expression, by both RNA-seq and qPCR array as well as increased pERK1/2 levels by WES. The compensatory response was tested with dual treatment with TYK2 and MEK inhibitors, which synergistically decreased proliferation and increased apoptosis in vitro. Finally, combination therapy was shown to inhibit growth of MPNST in multiple in vivo models.

These data provide the preclinical rationale for the development of a phase 1 clinical trial of deucravacitinib and mirdametinib in NF1-associated MPNSTs.

Introduction

Malignant Peripheral Nerve Sheath Tumors (MPNST) are aggressive sarcomas that often arise in people with Neurofibromatosis Type I (NF1), the most common cancer predisposition syndrome. Individuals with NF1 have one mutated copy of the NF1 gene, increasing the risk of developing benign plexiform neurofibromas (PN), which can later undergo malignant transformation to MPNST. The NF1 gene codes for neurofibromin, a tumor suppressor that is a negative regulator of RAS. Approximately half of MPNST cases occur in patients with NF1 while the other half occur sporadically or as a secondary complication of radiation therapy. In addition to NF1, the genes encoding CDKN2A, TP53, EED, and SUZ12 are frequently altered in MPNST. Despite aggressive treatments including surgery, chemotherapy and radiation, these cancers recur in about 50% of individuals and the majority of patients die within 5 years of their diagnosis. Currently, there are no effective treatments for patients with metastatic disease, thus, necessitating development of more efficacious targeted therapies for MPNST.

Genomic screening was previously conducted using next generation sequencing (NGS) and activating mutations were identified in tyrosine kinase 2 (TYK2) in a small subset of NF1-associated MPNST. However, by immunohistochemistry, TYK2 was found to be highly expressed in the majority of MPNST. A member of the Janus kinase (JAK) family of proteins, TYK2 is a receptor-associated kinase that mediates cytokine signaling through phosphorylation of signal transducers and activators of transcription (STAT) proteins. STATs subsequently translocate to the nucleus to regulate the transcription of over 300 target genes, including those involved in cancer cell proliferation, apoptosis, survival, and invasion. In subsequent studies, knockdown of the TYK2 gene was reported to reduce MPNST cell proliferation and increase cell death. TYK2 deficiency led to the decreased activation of downstream targets, including STAT1 and STAT3. Furthermore, TYK2 genetic knockdown also decreased MPNST tumor growth and metastasis in mice.

As an intermediary of immune system and inflammatory cytokines, TYK2 overexpression and hyperactivation promotes development and metastasis of multiple types of cancer, including leukemia, lymphoma, colorectal, breast, cervical, and prostate cancers. In line with this, genomic profiling of over 100 advanced sarcoma samples reveals mutations in TYK2, JAK1, JAK2, and JAK3. Pharmacological inhibitors of JAKs, including TYK2, have been developed clinically for autoimmune diseases, such as inflammatory bowel disease, psoriasis, and rheumatoid arthritis. Ruxolitinib and other pan-JAK inhibitory drugs (JAKinibs) are also FDA-approved or in clinical trials for treatment of various hematological cancers. In addition, several specific TYK2 inhibitors (TYKinibs) block growth of leukemia and solid cancer tumors in mice. However, intrinsic or acquired resistance to JAK or TYK2 inhibitors can lead to treatment failure in cancer. Combination strategies with JAKinibs or TYKinibs have been evaluated preclinically to overcome resistance and improve efficacy, including with the addition of chemotherapy agents or inhibitors targeting heat shock protein 90 (HSP90), histone deacetylase (HDAC), mammalian target of rapamycin (mTOR), or mitogen-activated protein/extracellular signal-regulated kinase (ERK) kinase (MEK). Many of these pathways are also activated in MPNST.

In MPNST, RAS overactivation due to loss of neurofibromin can lead to downstream activation of the RAF/MEK/MAP-kinase (MAPK) pathway, which can stimulate cancer cell proliferation, migration, and invasion. In addition to phosphorylated ERK1/2 protein levels, emerging evidence indicates that expression of a panel of signature genes, including SPRED1, SPRY2/4, and CCDN1, are more representative of activation of the Raf/MEK/MAPK pathway. Additionally, MEK inhibitors, such as mirdametinib and selumetinib, are showing therapeutic promise in preclinical and clinical trials for precursor benign PN as well as advanced MPNST.

In this study, the efficacy of small molecule TYK2 inhibitors was evaluated and signaling pathways downstream of TYK2 in MPNST were examined to identify potential targets for combination drug therapy. Herein, it was found that pharmacologic inhibition of TYK2 dose-dependently decreased cell proliferation and increased apoptosis in MPNST cells. Additionally, TYK2 inhibitors reduced STAT3 activation, while increasing ERK activation and expression of MEK/MAPK pathway target genes. Combination treatment with a TYK2 inhibitor and a MEK inhibitor synergistically blocked proliferation in MPNST, thus improving therapeutic efficacy and allowing for lower doses of each drug. Finally, it was demonstrated that combination therapy with clinically available TYK2 and MEK inhibitors markedly reduced MPNST tumor growth in mice.

Results

TYK2 is Expressed in the Majority of MPNST

Figures 1A, 1B:
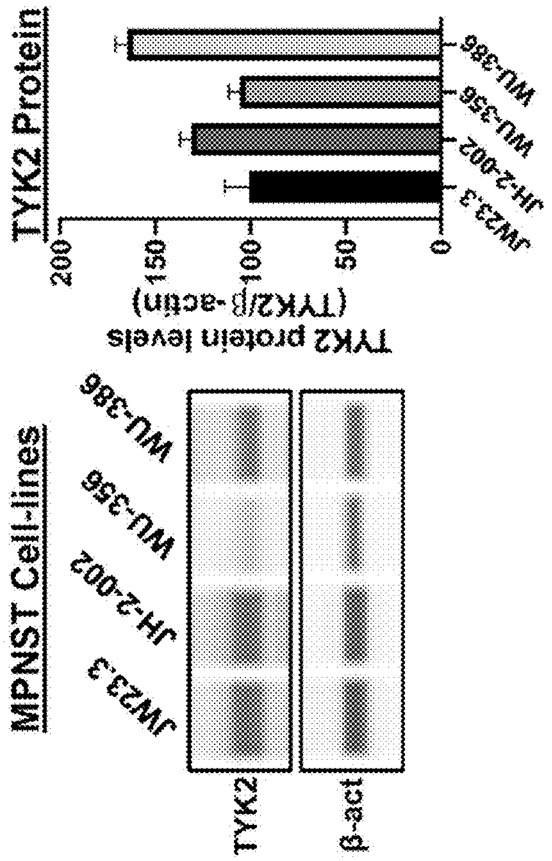
FIG. 1A is a table showing TYK2 protein levels visualized by immunohistochemistry (IHC) in MPNST and plexiform neurofibroma, with positive staining scored on a 0-3 scale.
FIG. 1B is a graph showing relative TYK2 protein levels in MPNST cell lines by WES western analysis. Protein bands analyzed by densitometry, with TYK2 normalized to β-actin.

IHC was conducted for TYK2 protein levels in 112 primary patient MPNST and 39 PN tumor samples. Strong TYK2 staining (score 2) was observed in 56% of high-grade MPNST samples, with 44% having weak or negative TYK2 staining (see e.g., FIG. 1A). In contrast, benign precursor PN were largely weak or negative for TYK2 (67%) (see e.g., FIG. 1A). Patient characteristics are detailed in TABLE

TABLE 1

Patient characteristics for TYK2 immunohistochemistry.

| Characteristics | MPNST TYK2 Strong (Proportion >= 2) | MPNST TYK2 Weak (Proportion < 2) | MPNST | Plexiform Neurofibromas |
|---|---|---|---|---|
| Sex no. (%) | | | | |
| Male | 23 | 26 | 49 | 21 |
| Female | 40 | 23 | 63 | 18 |
| Age Category no. (%) | | | | |
| <18 yo | 6 | 7 | 13 | 16 |
| 18-65 yo | 55 | 38 | 93 | 23 |
| >65 yo | 1 | 3 | 4 | 0 |
| Unknown | 1 | 1 | 2 | 0 |
| NF Status no. (%) | | | | |
| NF1 | 37 | 33 | 70 | 39 |
| Sporadic | 26 | 16 | 42 | 0 |

TYK2 protein expression was also verified in four MPNST cell lines (JW23.3, JH-2-002, WU-356 and WU-386) by the WES western system. All cell lines had moderate to high levels of TYK2 protein (see e.g., FIG. 1B).

TYK2 Inhibitors Decrease MPNST Cell Proliferation

Figure 1C:
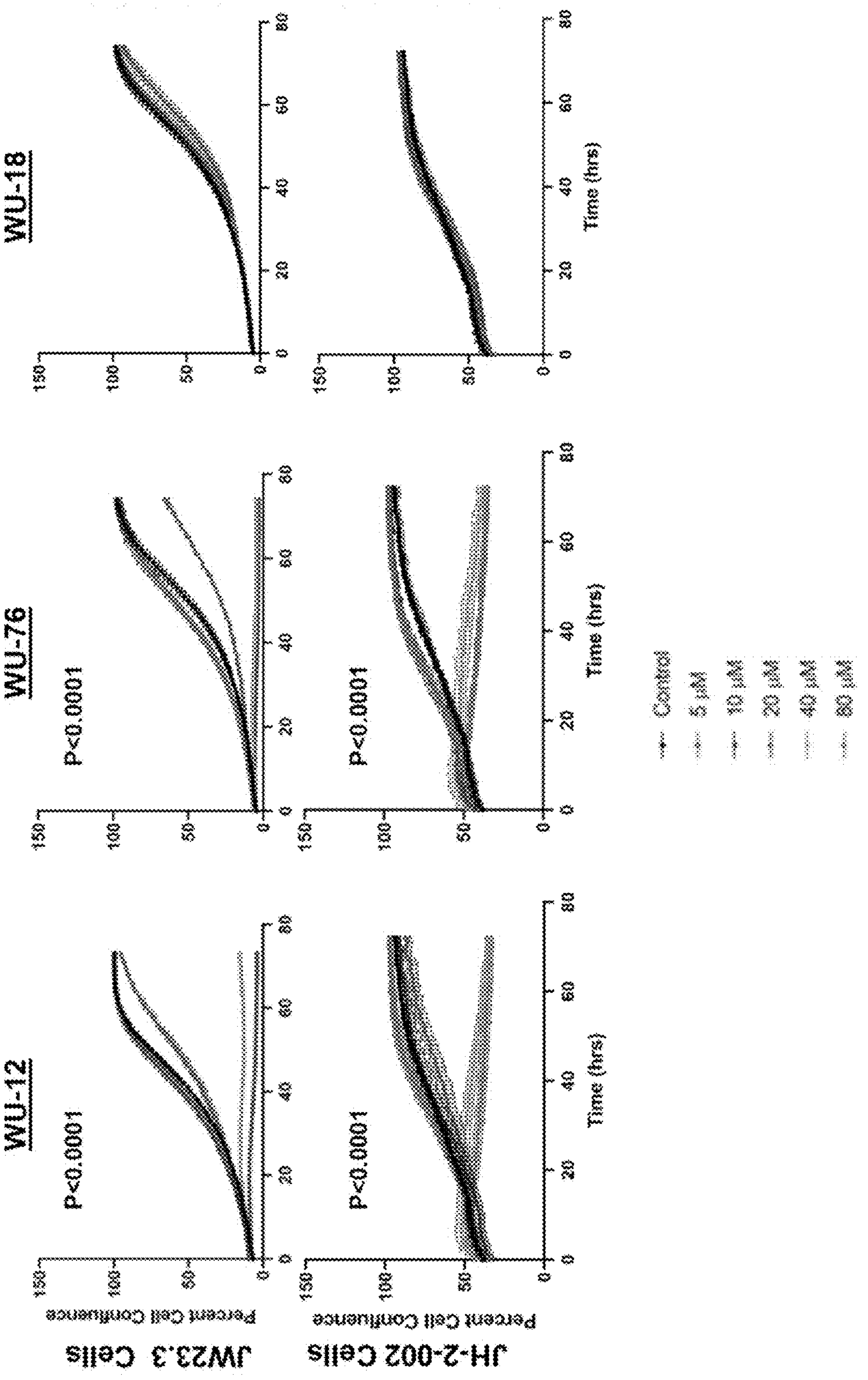
FIG. 1C includes graphs showing cell confluence of JW23.3 and JH-2-002 cells treated with TYK2 inhibitors (WU-12, WU-76) or inactive control (WU-18) for 3 days. Cell confluence was determined by IncuCyte assay.
Figure 1D:
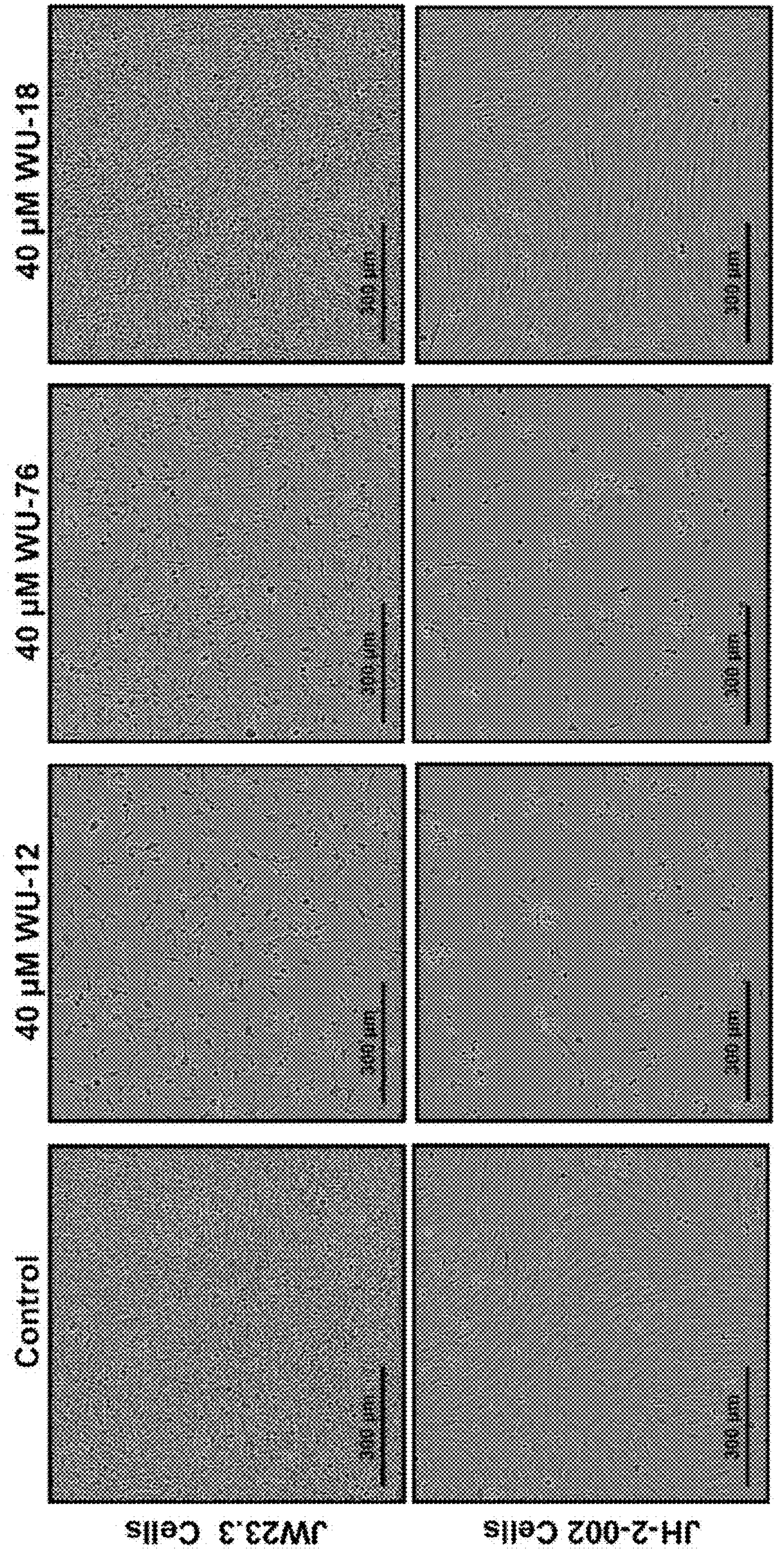
FIG. 1D includes representative images of IncuCyte assay at 72 hours, with YOYO-1 green fluorescence as indicator of apoptosis.
Figure 2A:
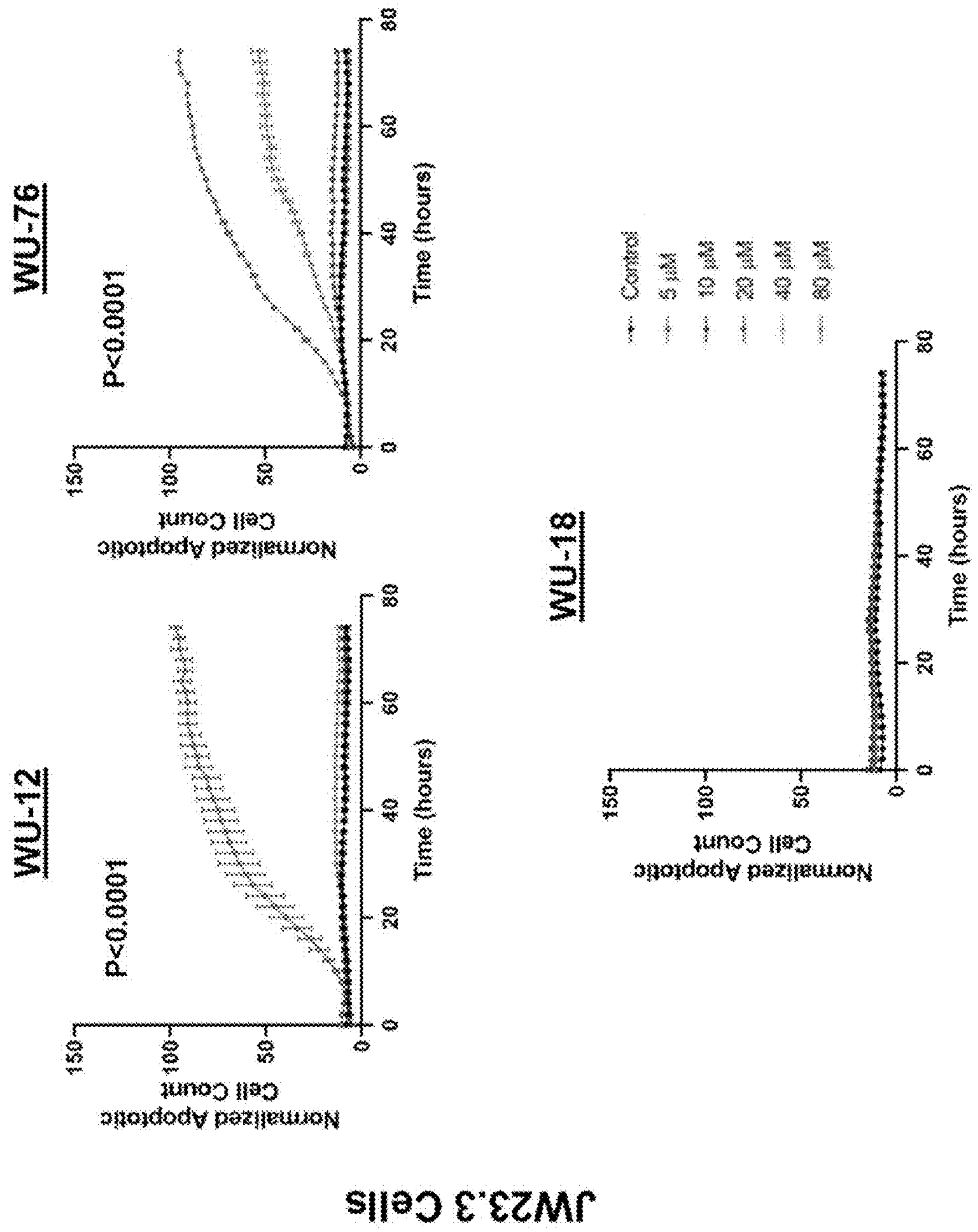
FIG. 2A shows apoptotic cell count of JW23.3 cells
Figure 2B:
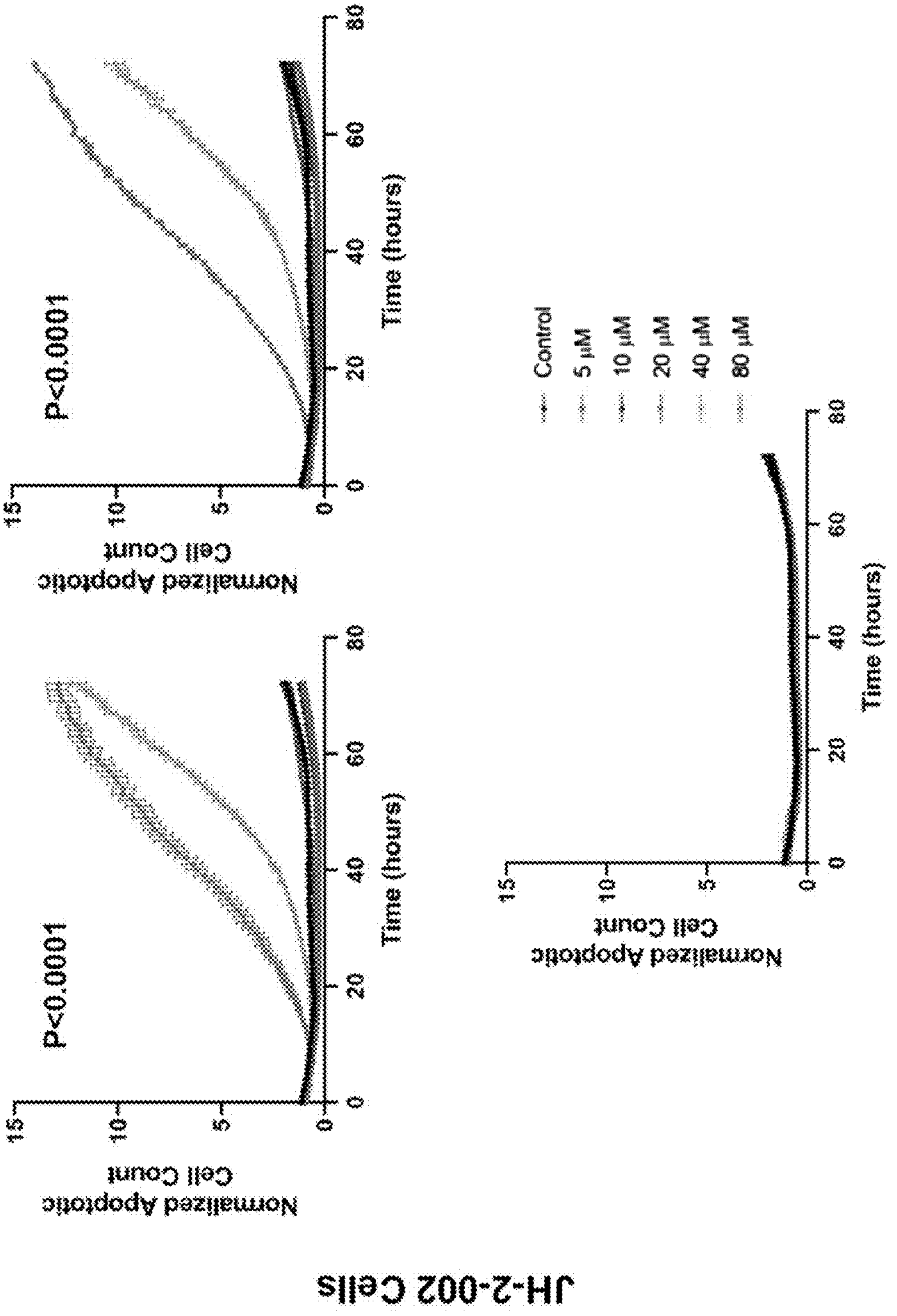
FIG. 2B shows apoptotic cell count of JH-2-002 cells incubated for 72 hours with TYK2 inhibitors, WU-12, or WU-76, or with an inactive control compound, WU-18. The IncuCyte cell death assay with YOYO-1 green fluorescent dye was used to measure apoptosis in cells over time. Apoptotic cell count was normalized to percent cell confluence over time. $^*P<0.0001$ vs. control.
Figure 3A:
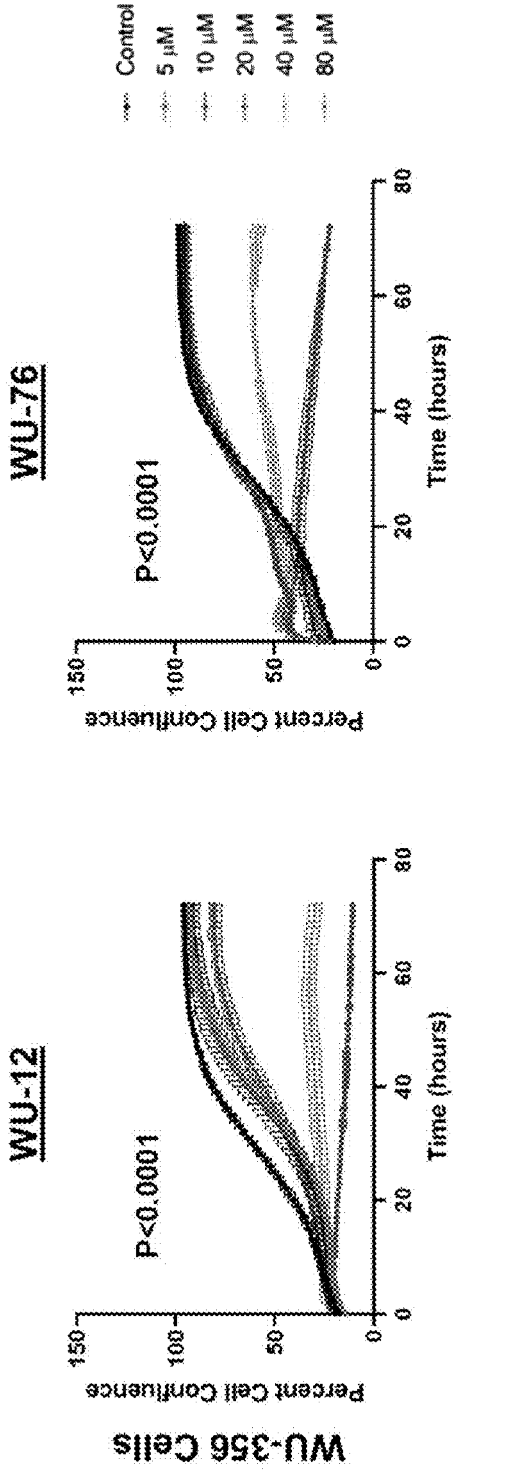
FIG. 3A shows confluence of WU-356 cells and FIG. 3B shows confluence of WU-386 cells treated with the indicated doses of TYK2 inhibitors, WU-12 (left panels)
Figure 3B:
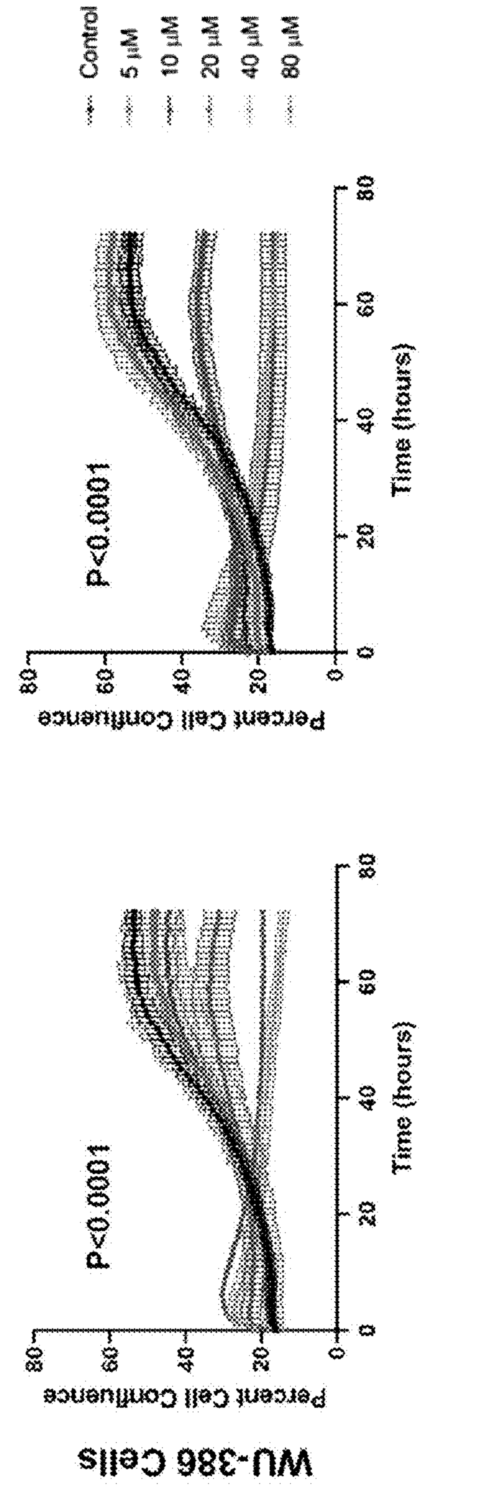

To gain further insight into the role of TYK2 in MPNST, the effect of pharmacologic inhibition of TYK2 was examined using IncuCyte Live Cell Imaging experiments for proliferation and cell death assay with YOYO-1 green fluorescent dye. Murine JW23.3 and human JH-2-002 MPNST cell lines were incubated for 72 hours with novel specific TYK2 inhibitor compounds developed at Washington University (compounds according to Formulas I and II, including WU-12 and WU-76, respectively) or an inactive control compound (WU-18) (see e.g., FIG. 1C-FIG. 1D). WU-12 and WU-76 dose-dependently decreased the percent cell confluence and increased apoptosis, while WU-18 had no effect, in either MPNST cell-line (see e.g., FIG. 1C-FIG. 1D and FIG. 2A-FIG. 2B). Representative pictures of both cell-lines after incubation with the TYK2 inhibitors for 3 days are shown in FIG. 1D. Similarly, in two additional human MPNST cell lines, WU-356 and WU-386, treatment with WU-12 and WU-76 reduced proliferation, indicating inhibition of TYK2 is generally effective in MPNST and is not just specific to a single cell line (see e.g., FIG. 3A-FIG. 3B and TABLE 2).

TABLE 2

IC50 concentrations for drugs inhibiting TYK2 in MPNST cell lines.

| MPNST Cell-line | Drug | IC50 |
|---|---|---|
| JW23.3 | WU-12 | 27.7 μM |
| JW23.3 | WU-76 | 18.7 μM |
| JH 2-002 | WU-12 | 26.5 μM |
| JH 2-002 | WU-76 | 30.8 μM |
| WU-356 | WU-12 | 39.8 μM |
| WU-356 | WU-76 | 40.2 μM |
| WU-386 | WU-12 | 20.2 μM |
| WU-386 | WU-76 | 21.7 μM |

IC50 values were calculated for inhibition of cell confluence by the TYK2 inhibitors in each cell-line, and ranged from 18.7-40.2 μM for JW23.3, JH-2-002, WU-356 and WU-386 cells (see e.g., TABLE 2).

TYK2 Inhibitors Stimulate the MEK/MAPK Pathway

Next, the impact of TYK2 downregulation on gene expression changes was examined using a high throughput qPCR array targeted for JAK-STAT pathway-related genes. Human JH-2-002 cells were incubated with a TYK2 inhibitor, WU-12, or vehicle control (DMSO) for 48 hours (see e.g., FIG. 4A). A qPCR array was utilized to analyze changes in mRNA for 88 genes of interest (GOIs) known to be downstream to the JAK-STAT pathway. Gene expression changes revealed a general upregulation of the MEK/MAP-kinase pathway (see e.g., FIG. 4A). TYK2 inhibition significantly increased MAPK pathway target gene expression, including Sprouty 4 (SPRY4), SPRED1 and Cyclin D1 (CCDN1), while decreasing inhibitors of the MAPK pathway, including CBL and CBLB. Members of the P13K/AKT/mTOR pathway that were decreased with TYK2 blockade included PIK3R3 and SOS1/2 (see e.g., FIG. 4A). WU-12 incubation also had variable effects on interleukins (IL) and related genes, including increasing IL7R, and IL6R, while decreasing IL7, IL10RB, and oncostatin M receptor (OSMR) (see e.g., FIG. 4A). Changes in expression of select genes identified by the qPCR array were then validated by qPCR using unique PCR primers pairs (data not shown).

Global Gene Expression Changes with TYK2 Inhibition

In order to determine the impact of TYK2 downregulation on the global expression profile of MPNSTs, RNA-seq experiments were conducted using specific TYK2 inhibitors, WU-12, and WU-76. RNA was isolated from JW23.3 cells treated with vehicle control (DMSO), WU-12 or WU-76 for 48 hours and the impact of TYK2 inhibition on the global expression profile was determined by RNA-seq. Pathway analysis revealed that inhibition of TYK2 stimulated GPCR pathways, MEK/MAPK signaling, and Oxidative Phosphorylation, while decreasing Cell Cycle, Mitotic, and Glycolysis pathways (see e.g., FIG. 4B). Down-regulated genes involved in proliferation and the G1 to S phase transition include Ccnd2, Cdkn1a/c, E2f3/4, Pole2 and Mcm7. In line with the qPCR array experiment (see e.g., FIG. 4A), incubation with TYK2 inhibitors increased expression of genes in the MEK/MAP-kinase pathway, e.g., Map3k2/3, MAP2k2/4, Map2, CD274, and Dusp4. These experiments provide important insight on the mechanism of TYK2 inhibitor action in MPNST and potential pathways that could be targeted in combination treatments in order to improve therapeutic efficacy.

TYK2 Blockade Lowers pSTAT3 while Raising pERK1/2 Levels

Next, the effects of TYK2 inhibition on STAT and MEK activation were validated by WES. In MPNST, the loss of neurofibromin leads to overactivation of Ras and downstream activation of MEK/MAPK. To investigate the interaction of TYK2 on these signaling pathways, the activation of STAT3 and ERK was evaluated in MPNST cells using the ProteinSimple WES system. In JW23.3 and JH-2-002 cells, the TYK2 inhibitor WU-12 decreased pSTAT3 protein levels at 1, 24 and 48 hours, as evaluated by the WES western blotting system (see e.g., FIG. 5A-FIG. 5B). Interestingly, pERK2 levels were strongly stimulated by 2-4-fold over time by treatment with the TYK2 inhibitors (WU-12) at 1 to 48 hours in the MPNST cell-lines, suggesting that the cells are compensating for TYK2 suppression by rapidly upregulating the MEK/ERK pathway, and this increase is sustained over several days. Thus, TYK2 inhibition induced a rapid and sustained increase in pERK1/2 protein levels and MEK/MAP-kinase pathway target gene expression, which may be a compensatory mechanism (see e.g., FIG. 5A-FIG. 5B).

A Clinically Relevant TYK2 Inhibitor, Deucravacitinib, Decreases MPNST Cell Proliferation In order to expedite translation to the clinic, a specific TYK2 inhibitor, deucravacitinib (BMS-986165), was subsequently tested. Deucravacitinib is used clinically in patients with autoimmune conditions, and the FDA recently approved deucravacitinib for treatment of plaque psoriasis. The TYK2 inhibitor, deucravacitinib, dose-dependently reduced JW23.3 cell proliferation with an IC50 value of 6.76 μM (see e.g., FIG. 6A). In addition, deucravacitinib inhibited proliferation of JH-2-002, WU-356 and WU-386 cells (see e.g., FIG. 6B-FIG. 6D).

MEK Inhibition Acts Synergistically with TYK2 Inhibition in MPNST

Based on the data demonstrating that inhibition of TYK2 stimulates the MEK/MAPK pathway in what may be a compensatory mechanism for the cancer cells (see e.g., FIG. 4A-FIG. 4B and FIG. 5A-FIG. 5B), it was investigated whether adding a MEK inhibitor improved the efficacy of TYK2 inhibition in MPNST. Single agent treatment of JW23.3, JH-2-002, WU-356 and WU-386 cells with a MEK1/2 inhibitor, mirdametinib (PD-0325901), dose-dependently reduced cell confluence percentage over 3 days, with an IC50 of 0.22-1.33 μM (see e.g., TABLE 3).

TABLE 3

IC50 concentrations for mirdametinib, a drug inhibiting MEK, in MPNST cell lines.

| MPNST Cell-line | Drug | IC50 |
|---|---|---|
| JW23.3 | Mirdametinib (PD0325901) | 1.22 μM |
| JH 2-002 | Mirdametinib (PD0325901) | 0.22 μM |
| WU-356 | Mirdametinib (PD0325901) | 1.33 μM |

TABLE 3-continued

| IC50 concentrations for mirdametinib, a drug inhibiting MEK, in MPNST cell lines. | | |
|---|---|---|
| MPNST Cell-line | Drug | IC50 |
| WU-386 | Mirdametinib (PD0325901) | 1.06 μM |

When mirdametinib was combined with the TYK2 inhibitor, deucravacitinib, in JW23.3 cells, the two drugs synergistically inhibited cell proliferation and increased apoptosis over either drug alone, with significant mean synergy scores of approximately 10 (see e.g., FIG. 7A-FIG. 7C). Deucravacitinib and mirdametinib also acted synergistically in JH-2-002 cells (see e.g., FIG. 8A-FIG. 8C). Similarly, combination treatment with a different TYK2 inhibitor, WU-12, and mirdametinib synergistically blocked proliferation in JW23.3 cells (see e.g., FIG. 9A-FIG. 9C). The synergistic actions of TYK2 and MEK inhibitors in vitro suggest that this combination would allow effective treatment in vivo with lower doses of each drug.

Combination TYK2 and MEK Inhibition Blocks MPNST Tumor Growth In Vivo

Figure 10A:
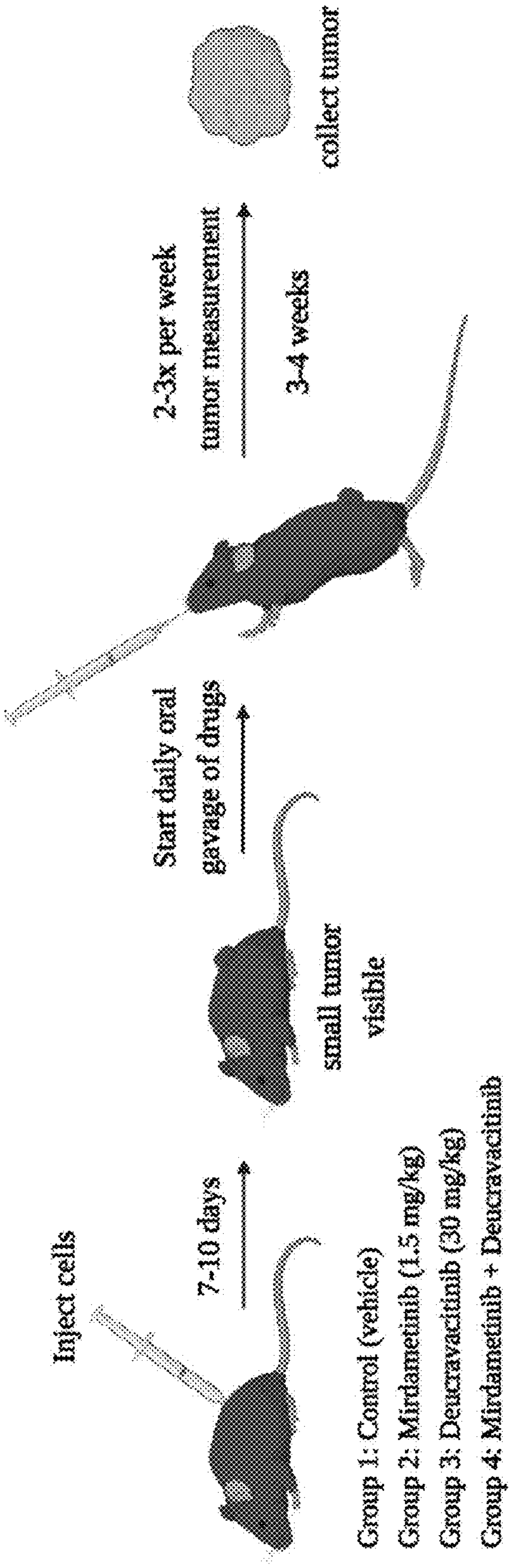
Figure 10B:
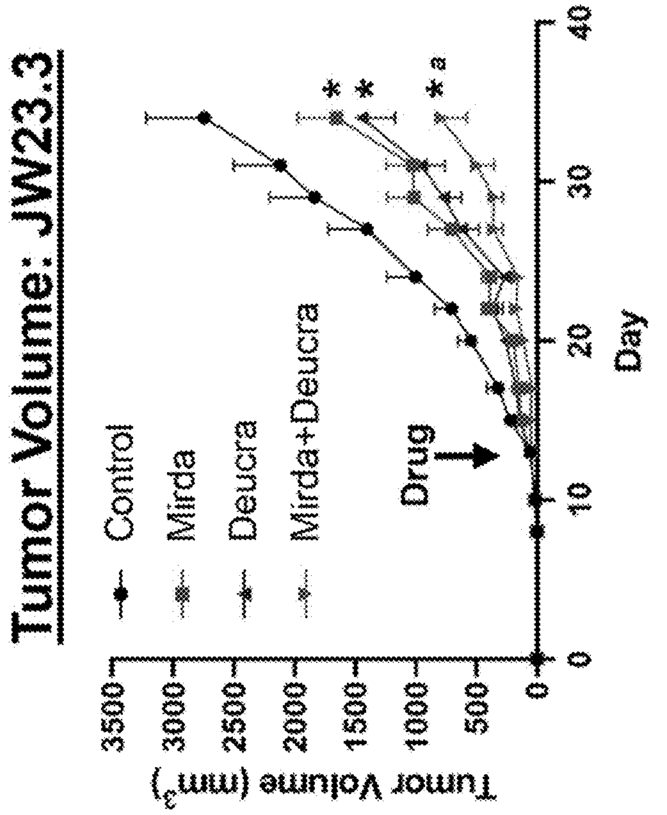
Figure 10C:
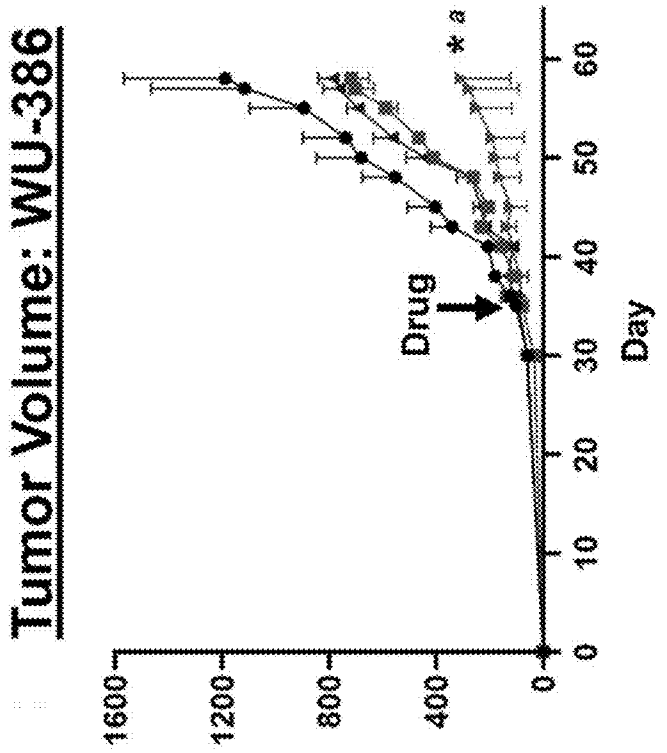
Figure 10D:
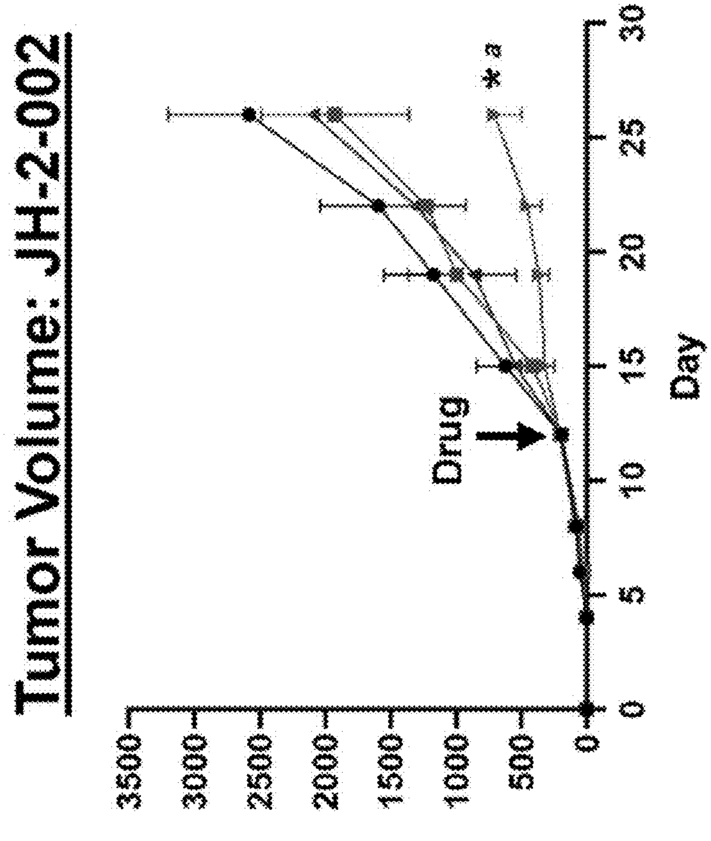

Based on the above data, the combination of TYK2 and MEK inhibitors on mice with MPNST xenograft tumors was examined in vivo (see e.g., FIG. 10A). In immunocompetent mice implanted with murine JW23.3 MPNST cells, treatment with mirdametinib, a MEK inhibitor, or deucravacitinib, a TYK2 inhibitor, significantly reduced tumors to nearly half the volume of vehicle control (see e.g., FIG. 10B). Consistent with in vitro synergy studies, the combination of mirdametinib and deucravacitinib decreased tumor growth to less than one-third of control and was significantly less than either drug alone (see e.g., FIG. 10B). In line with this, the drug combination of mirdametinib and deucravacitinib also inhibited human WU-386 MPNST xenograft tumor growth to about 25% of control and significantly less than with single agents (see e.g., FIG. 10C). For treatment with mirdametinib or deucravacitinib on their own, there was a non-significant trend toward decreased tumor size (see e.g., FIG. 10C). In a third tumor model using human JH-2-002 MPNST xenografts, combination TYK2 and MEK inhibition significantly blocked tumor growth compared to control or either drug alone (see e.g., FIG. 10D). Mice given the mirdametinib/deucravacitinib drug combination did not significantly lose weight or show adverse health effects in any of the mouse models (see e.g., FIG. 11A-FIG. 11C). Thus, the combination of drugs inhibiting TYK2 and MEK acted synergistically to improve the therapeutic efficacy in both murine and human MPNST models.

Discussion

Therapeutic options are limited for MPNST, thus necessitating development of novel treatment strategies. Previous work identified high expression of TYK2 in more than two-thirds of MPNST samples, suggesting that this protein could be a potential drug target for a high proportion of MPNST. There are several key findings in the study presented herein. First, multiple pharmacological inhibitors of TYK2 were shown to reduce proliferation and increase apoptosis in a panel of murine and human MPNST cell lines.

Deucravacitinib (BMS-986165), a highly specific second-generation TYK2 inhibitor, targets the JH2 pseudokinase domain of the TYK2 protein and is FDA-approved for the treatment of plaque psoriasis. Unlike first-generation TYKinibs directed against the catalytic JH1 domain, which shares overlapping homology amongst all JAKs, deucravacitinib does not block JAK1-3 at clinically relevant doses. In plaque psoriasis, the actions of deucravacitinib are mediated through inhibition of type I interferon (IFN), interleukin-12 (IL-12), and IL-23 signal transduction. In MPNST, it remains unclear as to what upstream proteins are relevant.

Due to their immunosuppressive properties, selective inhibitors of JAKs (JAK1-3 and TYK2) were initially utilized for treatment of autoimmune diseases. However, these drugs are also being explored in the oncology space. JAKinibs, including ruxolitinib, fedratinib, momelotinib, have been approved as therapeutics for hematological cancers, and the JAK2 inhibitor AZD1480 is in clinical trials for solid cancers. In addition, first and second-generation TYKinibs (e.g., SAR-20347, SAR-20351 and NDI-031301) show promise in preclinical studies for treatment of blood and solid tumor malignancies. However, regulators have recently limited use of some inhibitors directed against JAK1-3 after reports of serious adverse events, thus increasing interest in development of specific TYK2 inhibitors. Since deucravacitinib does not bind to other JAKs, it may have a safer side effect profile compared to inhibitors directed against JAK1-3.

Second, in this study, it was demonstrated that TYK2 inhibition decreased pSTAT3 levels while stimulating activation of the MEK/MAPK pathway in what is likely a compensatory survival mechanism for the cancer cells. This is in line with studies in other types of cancer, in which intrinsic or acquired resistance over time to JAKinib/TYKinib may result in treatment failure and poor outcomes. Drug resistance is common in patients with hematological malignancies treated with ruxolitinib, a pan-JAK inhibitor, for two to three years. Similarly, leukemia cells can develop resistance with protracted exposure to cerdulatinib, a pan-JAK/TYK2 inhibitor. Insensitivity to JAK and TYK2 inhibitors may be the result of heterodimerization with other JAK family members, subsequently acquired mutations in the JAK/TYK2 kinase domain that interfere with drug binding, activation of other signaling pathways (e.g., RAS, MAPK, and Akt pathways), or mutations in epigenetic regulatory genes. In an effort to overcome resistance to TYK2 and JAK inhibitors, combination therapies have been investigated, including with histone deacetylase inhibitor (HDACi), heat shock protein 90 (HSP90) inhibitors, chemotherapy drugs, MEK inhibitors, mTOR inhibitor, or a second JAK inhibitor.

In this current study, signaling pathways downstream of TYK2 and changes in global gene expression in MPNST cells were investigated to identify additional targets for possible combination drug therapy. The mechanism of TYK2 signaling was evaluated via several complementary methods, including western analysis for protein activation, RNA-seq for global gene expression, and a high throughput qPCR array for expression of genes known to be downstream of JAK/STAT family members. These results detected significant changes in genes and proteins involved in cell cycle, inflammation, immune function, and cancer signaling. At the protein level, TYK2 inhibitor drugs lowered STAT3 activation, while increasing ERK1/2 activation at 1-48 hours (see e.g., FIG. 5A-FIG. 5B). This indicates rapid signal transduction at the protein level, as well as long-term, sustained gene expression changes affecting the MEK/MAPK pathway. However, the exact signaling molecules mediating the direct crosstalk of TYK2 inhibition to elevate pERK1/2 in the short-term is unclear. In addition, the MEK/MAPK pathway is complex, and levels of ERK1/2 phosphorylation do not always provide the overall view of activation of the MEK/MAPK pathway. MEK/MAPK gene expression signature profiles have been previously reported using the MEK inhibitors selumetinib and mirdametinib. Consistent with these MEK/MAPK pathway gene signatures, the qPCR array and RNAseq data herein show that TYK2 inhibitors (e.g., compounds according to Formula I such as WU-12, compounds according to Formula II such as WU-76, and deucravacitinib) stimulated gene expression in the MEK/MAPK pathway, including SPRY4, SPRED1, CCDN1, Map3k2/3, MAP2k2/4, Map2, CD274, and Dusp4 (see e.g., FIG. 4A-FIG. 4B). Other reports have indicated that treatment with JAK inhibitors may induce the MEK/MAPK pathway in myoproliferative neoplasms and melanoma in preclinical in vitro and in vivo studies. Conversely, MEK inhibitors increase the JAK/STAT pathway in melanoma cells, indicating crosstalk between the two pathways, and co-incubation of a JAK inhibitor with a MEK inhibitor greatly improves treatment efficacy in melanoma. MEK inhibitors, including selumetinib and mirdametinib, are used clinically for benign PN as well as advanced MPNST. However, MPNST frequently develop resistance to kinase inhibitor drugs, including MEK inhibitors, with long-term treatment. Despite promising preclinical studies, single agents, including MEK inhibitors, mTOR inhibitors, and HSP90 inhibitors, have had limited success in MPNST treatment in patients, likely due to adaptive survival responses. Indeed, in the study herein, single agent therapy with a MEK inhibitor, mirdametinib, only moderately reduced tumor growth in vivo (see e.g., FIG. 10A-FIG. 10D and FIG. 12A-FIG. 12B).

Finally, addition of mirdametinib, a MEK inhibitor, synergistically enhanced the efficacy of deucravacitinib, a TYK2 inhibitor, in MPNST cells in vitro and on MPNST tumor growth in three in vivo mouse models (see e.g., FIG. 7A-FIG. 7C, FIG. 10A-FIG. 10D, and FIG. 12A-FIG. 12B). A schematic diagram of the proposed signaling actions of TYK2 and/or MEK inhibitors in MPNST is shown in FIG. 12A-FIG. 12B. Development of drug combination strategies aims to improve therapeutic efficacy in MPNST patients, resulting in longer survival and increasing the treatment options available for this aggressive cancer. Taken together, these data provide the preclinical rationale for the development of a phase 1 clinical trial of deucravacitinib and mirdametenib in NF1-associated MPNSTs.

Methods

Cell Culture

Human MPNST cell-lines were generated at Johns Hopkins University (JH-2-002 cells), and obtained through the NTAP biobank, or generated from MPNST PDX lines at Washington University (WU-356 and WU-386). Murine MPNST JW23.3 cells were established previously from C57BL6/J Nf1+/−; Trp53+/−cis (NPcis) mice. Cells were cultured in growth media including Dulbecco's Modified Eagle Medium High Glucose (DMEM) with 10% Fetal Bovine Serum (FBS, Gibco Life Technologies, ThermoFisher) and penicillin-streptomycin (200 μg/mL, ThermoFisher). WU-356 and WU-386 cells were grown in RPMI containing 20% FBS and penicillin-streptomycin (200 μg/mL) on matrigel-coated dishes. Cell cultures were maintained at 37° C. and 5% $CO_2$.

Cell Proliferation and Apoptosis Assays

MPNST cell lines were plated at 2500 cells/well in 96 well plates in growth media and incubated overnight. Cells were then treated for 72-96 hours in phenol-red free media containing 5% FBS, with various doses of WU-12, WU-76, WU-18, deucravacitinib (MedChemExpress), and/or mirdametinib (Springworks). Cells were imaged every 1-2 hours by IncuCyte Zoom Live-Cell Analysis System (Essen Bioscience, Sartorius, Ann Arbor, MI). Cell proliferation was determined as percent confluence from phase images and was analyzed by IncuCyte image analysis software (Sartorius). For cell death assays, 50 nmol/L YOYO-1 green fluorescent dye (Thermo Fisher) was added to treatment medium, and apoptosis was calculated as green objects normalized to the confluency factor and the initial timepoint. IC50 values were calculated in GraphPad Prism version 9 (GraphPad Software, San Diego, CA).

Immunohistochemistry (IHC)

Formalin-fixed paraffin-embedded (FFPE) slides of MPNST, PN, and ANNUBP tumors were obtained from Washington University, John Hopkins University (JHU), the National Cancer Institute (NCI), and the University of California at San Francisco (UCSF). The institutional review board (IRB) approved the use of de-identified patient samples. Immunostaining for TYK2 was performed on 112 MPNST and 39 PN. Sections were first deparaffinized and rehydrated, followed by antigen retrieval in sodium citrate buffer for 15 minutes and blocking in 3% $H_2O_2$ and avidin/biotin. After blocking, the sections were incubated with TYK2 primary antibody (Abcam, ab223733, 1:100) overnight, followed by anti-rabbit HRP-conjugated secondary antibody (1:200). Diaminobenzidine (DAB) was the chromogen with hematoxylin counterstaining. IHC staining was scored independently by three investigators (including board certified pathologist, CD) blinded to patient data with the proportion score (0: 0% TYK2 staining, 1: 1-33% TYK2 staining, 2: 34-66%, 3: 66% TYK2 staining) in 0.5 intervals.

Synergy Analysis for Drug Combination Studies

For synergy calculations of drug combinations, IncuCyte dose response data for cell proliferation or apoptosis, normalized to maximum inhibition values, were analyzed using SynergyFinder 2.0 software and the HSA model. The mean synergy score and a p-value were calculated for the entire matrix by SynergyFinder software. Synergy values>10 were considered synergistic, while −10 to 10 was additive, and <−10 was antagonistic.

RNA Isolation and Quantitative PCR

Total RNA was isolated using an RNeasy Mini kit (Qiagen), and genomic DNA was removed by adding DNase I for 15 minutes to the RNA samples. Total RNA concentrations were determined using a Nanodrop 2000 (ThermoFisher Scientific). cDNA was synthesized from total RNA using the High Capacity cDNA Reverse Transcription Kit (Applied Biosystems). Quantitative real-time PCR (qPCR) was performed using the Power SYBR Green Master Mix kit (Thermo Fisher) on the CFX96 Touch™ Real-Time PCR Detection System (Bio-Rad, USA). Relative gene expression was calculated using CFX Manager Software version 3.1 (Bio-Rad, USA), and values were normalized to housekeeping gene. Fold-changes in gene expression compared to control were calculated using the $2^{-\Delta\Delta Ct}$ method.

Western Analysis

MPNST cell lines were plated in 6-well plates at 200,000 cells/well in growth media, and the next day treated for the indicated times with WU-12, WU-76, deucravacitinib (Deucra) or vehicle control (DMSO). Cells were washed with 1× PBS and lysed in 1× Cell Lysis Buffer (Cell Signaling Technology). Equal amounts of protein were run on the WES capillary electrophoresis western system (ProteinSimple, Bio-Techne, Minneapolis, MN), following manufacturer protocol and standard instrument settings. Protein levels were analyzed using Compass SimpleWestern software (ProteinSimple). Primary antibodies included total STAT3 (4904S), pSTAT3 (9145S), total p44/42 ERK1/2 (4695S), pERK1/2 (4370S), total p70 S6K (2708S), pS6K (9205S), β-actin (all from Cell Signaling Technologies) and TYK2 (Abclonal). Phosphorylated protein levels were normalized to the respective total protein levels and expressed as a percent of control for each time point.

qPCR Pathway Array

The effect of TYK2 inhibition on gene expression of potential downstream targets known to be in the JAK-STAT pathway was assessed by a PrimerArray® Jak-STAT Signaling Pathway (Human) qPCR array in 96-well plate format (Takara Bio). JH-2-002 cells were plated in growth media in 6-well plates at a density of 200,000 cells per well. The next day, the cells were treated in triplicate with vehicle control (DMSO) or 40 μM TYK2 inhibitor WU-12, for 48 hours. RNA was isolated and cDNA synthesized as above. qPCR was performed with TB SYBR Green Premix Ex Taq II (Takara Bio) and the Jak-STAT primer arrays on the CFX96 PCR instrument, with gene expression assessed by CFX Manager Software. The PrimerArray Analysis Tool Version 2.2 software (Takara) was utilized for pathway analysis of 3 replicate plates per condition. Briefly, gene expression was normalized to 8 housekeeping genes and fold-change was expressed versus control using the ΔΔCT method. The PrimerArray includes primers for 88 JAK-STAT biological pathway related genes and 8 housekeeping genes.

Bulk RNA-Seq Analysis

JW23.3 cells were treated with 40 μM WU-12, 40 μM WU-76, or vehicle control (DMSO) for 48 hours. RNA was isolated as discussed above, and samples contained at least 5 ug of purified total RNA with RIN>9.0. At least three biological replicates were performed. Samples were aligned against Mouse Ensembl GRCm38.76. Total RNA integrity was determined using Agilent Bioanalyzer or 4200 Tapestation. Library preparation was performed with 5 to 10 ug of total RNA with a Bioanalyzer RIN score greater than 8.0. Ribosomal RNA was removed by poly-A selection using Oligo-dT beads (mRNA Direct kit, Life Technologies). mRNA was then fragmented in reverse transcriptase buffer and heating to 94 degrees for 8 minutes. mRNA was reverse transcribed to yield cDNA using SuperScript III RT enzyme (Life Technologies, per manufacturer's instructions) and random hexamers. A second strand reaction was performed to yield ds-cDNA. cDNA was blunt ended, had an A base added to the 3' ends, and then had Illumina sequencing adapters ligated to the ends. Ligated fragments were then amplified for 12-15 cycles using primers incorporating unique dual index tags. Fragments were sequenced on an Illumina NovaSeq-6000 using paired end reads extending 150 bases. Differential expression analysis was performed with the DESeq2 package (R Bioconductor software).

Animals

Mice were housed and treated in compliance with an approved protocol for the Institutional Animal Care and Use Committee (IACUC) of Washington University (Protocol #20-0117). For experiments with murine MPNST cells, 5-6-week-old C57BL6 mice (Taconic) were implanted with 400,000 JW23.3 cells subcutaneously (s.c.) on the dorsal surface. For experiments with human MPNST cells, 6-10-week-old immunodeficient NOD-Rag1$^{null}$ IL2rg$^{null}$ (NRG) mice (strain #007799, Jackson Laboratories) were implanted on the s.c. dorsal surface with a single cell suspension of WU-386 cells ($3\times10^6$ cells per mouse) or JH-2-002 cells ($1\times10^6$ cells per mouse). Tumors were monitored by calipers two to three times per week, and tumor volume was calculated as volume=0.52×length×width×width. Drug treatments were initiated when tumors reached tumors reached ~50-200 mm$^3$. Mice were given 30 mg/kg deucravacitinib (MedChemExpress, in 5% ethanol/5% TPGS/90% PEG300) and/or 1.5 mg/kg mirdametinib (SpringWorks Therapeutics, in 0.5% HPMC/0.2% Tween-80/water), or vehicle control daily via oral gavage for 3-4 weeks. Tumors were extracted, photographed, and weighed at the end of experiments.

Statistical Analysis

Data was analyzed and graphed in GraphPad Prism version 9. Data was expressed as mean±standard error of the mean (SEM). Two-way ANOVA or Student t-test were used to calculate statistical significance where appropriate. $P<0.05$ was considered significantly significant.

Example 2: TYK2 is a Biomarker and Therapeutic Target in Malignant Peripheral Nerve Sheath Tumors This Example describes TYK2 as a prognostic biomarker for MPNST, the oncogenic mechanisms of TYK2 in MPNST, and the utility of targeting TYK2 as a treatment strategy for MPNST.

Introduction

Malignant peripheral nerve sheath tumors (MPNST) are highly aggressive sarcomas with limited treatment options and poor survival rates. About half of MPNST cases are associated with the Neurofibromatosis Type 1 (NF1) cancer predisposition syndrome, while the other half occur sporadically or as a secondary complication of radiation therapy. In individuals with NF1, MPNST develop from benign plexiform neurofibromas (PN), however, there are no predictive biological markers of transformation. Despite therapies including surgery, chemotherapy and/or radiation, these tumors recur in about 50% of patients and most die within 5 years of diagnosis.

TYK2 was previously identified as a gene mutated in a subset of MPNST. More recently, it was shown that genetic knockdown of TYK2 in MPNST cell lines results in decreased proliferation and increased cell death in vitro. Additionally, Tyk2 knockdown in murine MPNST cells resulted in decreased tumor burden in subcutaneous and metastatic tumor models. Herein is described a study to: 1) determine whether TYK2 is a prognostic biomarker for MPNST and can distinguish MPNST from precursor lesions, 2) examine the oncogenic mechanisms of TYK2 in MPNST, and 3) evaluate the utility of targeting TYK2 as a treatment strategy for MPNST.

Methods

MPNST cell lines (JW23.3, MPNST-724, JH2-002, and JH2-009) were treated with inhibitors of MEK (mirdametinib) and/or TYK2 (compounds according to Formulas I and II (including WU-12 and WU-76, respectively), or TC-JL-37).

RNA was isolated by an RNeasy Minikit and cDNA synthesized using the High Capacity cDNART Kit. qPCR was performed with Power SYBR Green Master Mix kit on CFX96 PCR System (Bio-Rad).

Cell confluence and apoptosis were analyzed by IncuCyte live cell imaging assays. Drug combination synergy was calculated using Synergy Finder software.

Total and phosphorylated protein levels were examined by WES western blotting system (Protein Simple).

Gene expression changes were analyzed by a Primer Array JAK-STAT Signaling Pathway qPCR array in 96-well plate format (TakaraBio).

For RNAseq, an mRNA library was sequenced on an Illumina HISeq4000. Trimmed and aligned reads were analyzed and presented using R package: FGSEA, GSEA analysis, Deseq2, and pheatmap.

Immunohistochemistry (IHC) for TYK2 was performed on 60 MPNST, 39 PN, and 24 atypical neurofibromas (ANNUBP). Sections were sequentially incubated in antigen retrieval buffer, block, primary antibody, conjugated secondary antibody, DAB chromagen and hematoxylin counter stain.

Statistical significance ($p<0.5$) by ANOVA and t-tests.

Results

As shown herein, pharmacologic inhibition of TYK2 dose-dependently decreased the percent cell confluence and induced apoptosis over time in MPNST cell lines. For example, JW23.3 and 2-009 cells were treated with the TYK2 inhibitor TC-JL-37 over 3 days, which resulted in decreased cell confluence and increased apoptosis (see e.g., FIG. 13A-FIG. 13B).

TYK2 inhibition also led to compensatory stimulation of the MEK/MAP kinase (MAPK) pathway in MPNST cells, as shown in FIG. 14. Based on this result, JW23.3 MPNST cells were treated with TYK2 inhibitor WU-12 and MEK inhibitor mirdametinib. This combination results in a synergistic reduction in proliferation of the MPNST cells (see e.g., FIG. 15A-FIG. 15B).

Immunostaining revealed elevated TYK2 protein levels in MPNST vs. benign PN (see e.g., FIG. 16A-FIG. 16C). TYK2 protein levels were also increased in ANNUBP (atypical neurofibromatous neoplasms of uncertain biologic potential).

These findings suggest that TYK2 is a novel therapeutic target that promotes MPNST pathogenesis through STAT3 activation and inhibition of apoptosis.

Further, TYK2 expression is associated with MPNST and thus may serve as a biomarker for transformation to MPNST.

What is claimed is:

1. A method of treating cancer comprising administering a synergistic amount of a TYK2 inhibiting agent and an MEK inhibiting agent, wherein the TYTK2 inhibiting agent comprises at least one of deucravacitinib and WU-12 and the MEK inhibiting agent comprises mirdametinib; and wherein the cancer is malignant peripheral nerve sheath tumor (MPNST).

2. The method of claim 1, wherein the MPNST overexpresses TYK2 or comprises a TYK2 mutation.

3. The method of claim 1, wherein the subject has neurofibromatosis Type 1 (NF1) cancer predisposition syndrome, benign plexiform neurofibromas (PN), or atypical neurofibromas (ANNUBP).

4. The method of claim 1, wherein the TYK2 inhibiting agent does not inhibit JAK1, JAK2, or JAK3.

* * * * *